US008722657B2

(12) United States Patent
Catron et al.

(10) Patent No.: US 8,722,657 B2
(45) Date of Patent: May 13, 2014

(54) SALTS AND CRYSTALLINE FORMS OF AN APOPTOSIS-INDUCING AGENT

(75) Inventors: Nathaniel Catron, Vernon Hills, IL (US); Shuang Chen, Gurnee, IL (US); Yuchuan Gong, Waukegan, IL (US); Geoff G. Zhang, Vernon Hills, IL (US)

(73) Assignee: Abbvie Inc., North Chicago, IL (US)

( * ) Notice: Subject to any disclaimer, the term of this patent is extended or adjusted under 35 U.S.C. 154(b) by 69 days.

(21) Appl. No.: 13/301,257

(22) Filed: Nov. 21, 2011

(65) Prior Publication Data
US 2012/0157470 A1 Jun. 21, 2012

Related U.S. Application Data

(60) Provisional application No. 61/416,656, filed on Nov. 23, 2010.

(51) Int. Cl.
*A01N 43/00* (2006.01)
*A61K 31/397* (2006.01)
*A61K 31/497* (2006.01)

(52) U.S. Cl.
USPC ............. 514/210.01; 514/252.11; 514/254.09

(58) Field of Classification Search
None
See application file for complete search history.

(56) References Cited

U.S. PATENT DOCUMENTS

| | | | |
|---|---|---|---|
| 6,720,338 B2 | 4/2004 | Augeri et al. | |
| 6,787,534 B2 | 9/2004 | Haneda et al. | |
| 6,858,638 B2 | 2/2005 | Damour et al. | |
| 7,390,799 B2 | 6/2008 | Bruncko et al. | |
| 7,504,512 B2 | 3/2009 | Augeri et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,642,260 B2 | 1/2010 | Bruncko et al. | |
| 7,709,467 B2 | 5/2010 | Bruncko et al. | |
| 7,754,886 B2 | 7/2010 | Augeri et al. | |
| 7,767,684 B2 | 8/2010 | Bruncko et al. | |
| 8,084,607 B2 | 12/2011 | Bruncko et al. | |
| 8,173,811 B2 | 5/2012 | Bruncko et al. | |
| 8,187,836 B2 | 5/2012 | Hsieh | |
| 8,354,404 B2 | 1/2013 | Bruncko et al. | |
| 2002/0055631 A1 | 5/2002 | Augeri et al. | |
| 2003/0144507 A1 | 7/2003 | Haneda et al. | |
| 2005/0101628 A1 | 5/2005 | Jiao et al. | |
| 2005/0159427 A1 | 7/2005 | Bruncko et al. | |
| 2005/0208082 A1 | 9/2005 | Papas et al. | |
| 2006/0128706 A1 | 6/2006 | Bruncko et al. | |
| 2007/0015787 A1 | 1/2007 | Bruncko et al. | |
| 2007/0027135 A1 | 2/2007 | Bruncko et al. | |
| 2007/0072860 A1 | 3/2007 | Bruncko et al. | |
| 2008/0076779 A1 | 3/2008 | Elmore et al. | |
| 2008/0182845 A1 | 7/2008 | Bardwell et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2009/0176785 A1 | 7/2009 | Bardwell et al. | |
| 2010/0022773 A1 | 1/2010 | Bruncko et al. | |
| 2010/0152183 A1 | 6/2010 | Bruncko et al. | |
| 2010/0160322 A1 | 6/2010 | Bruncko et al. | |
| 2010/0184750 A1 | 7/2010 | Hexamer et al. | |
| 2010/0184766 A1 | 7/2010 | Kunzer et al. | |
| 2010/0227838 A1 | 9/2010 | Shah et al. | |
| 2010/0297194 A1 | 11/2010 | Catron et al. | |
| 2010/0298321 A1 | 11/2010 | Bruncko et al. | |
| 2010/0298323 A1 | 11/2010 | Bruncko et al. | |
| 2010/0305122 A1 | 12/2010 | Bruncko et al. | |
| 2011/0124628 A1 | 5/2011 | Bruncko et al. | |
| 2012/0108590 A1 | 5/2012 | Birtalan et al. | |
| 2012/0129853 A1 | 5/2012 | Elmore et al. | |
| 2012/0190688 A1 | 7/2012 | Bruncko et al. | |
| 2012/0277210 A1 | 11/2012 | Catron et al. | |

FOREIGN PATENT DOCUMENTS

| | | |
|---|---|---|
| EP | 1796642 | 5/2008 |
| RU | 2001103044 | 8/2003 |
| RU | 2239631 | 11/2004 |
| RU | 2004130280 | 6/2005 |
| RU | 2387653 | 4/2010 |
| WO | WO 9507271 | 3/1995 |
| WO | WO 9710223 | 3/1997 |

(Continued)

OTHER PUBLICATIONS

Berge, S. M. et al., "Pharmaceutical Salts," Journal of Pharmaceutical Sciences, 1977, vol. 66 (1), pp. 1-19.
Caira M.R., "Crystalline Polymorphism of Organic Compounds," 1998, vol. 198, pp. 163-208.
Hanahan D., et al., "The Hallmarks of Cancer," Cell, 2000, vol. 100 (1), pp. 57-70.
Holzelova, E. et al., "Autoimmune Lymphoproliferative Syndrome with Somatic Fas Mutations," New England Journal of Medicine, 2004, vol. 351 (14), pp. 1409-1418.
Kibbe A.H., ed., Handbook of Pharmaceutical Excipients, 3rd Edition, 2000, American Pharmaceutical Association, Table of Contents.
Puck J.M., et al., "Immune Disorders Caused by Defects in the Caspase Cascade ," Current Allergy and Asthma Reports, 2003, vol. 3, pp. 378-384.
Rengan R., et al., "Actin Cytoskeletal Function is Spared, but Apoptosis is Increased, in WAS Patient Hematopoietic Cells," Blood, 2000, vol. 95 (4), pp. 1283-1292.
Shimazaki K., et al., "Evaluation of Apoptosis as a Prognostic Factor in Myelodysplastic Syndromes," British J Haematology, 2000, vol. 110 (3), pp. 584-590.

(Continued)

*Primary Examiner* — Anna Pagonakis
(74) *Attorney, Agent, or Firm* — Jones Day

(57) ABSTRACT

Salts and crystalline forms of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}-sulfonyl)-2-(1H-pyrrolo[2,3-b]pyridin-5-yloxy)benzamide are suitable active pharmaceutical ingredients for pharmaceutical compositions useful in treatment of a disease characterized by overexpression of one or more anti-apoptotic Bcl-2 family proteins, for example cancer.

3 Claims, 14 Drawing Sheets

(56) References Cited

FOREIGN PATENT DOCUMENTS

| WO | WO 9729131 | 8/1997 |
|---|---|---|
| WO | WO 0001389 | 1/2000 |
| WO | WO 0057854 | 10/2000 |
| WO | WO 0100175 | 1/2001 |
| WO | WO0224636 A2 | 3/2002 |
| WO | WO 02066470 | 8/2002 |
| WO | WO 02098848 | 12/2002 |
| WO | WO2005049593 A2 | 6/2005 |
| WO | WO 2005049594 | 6/2005 |
| WO | WO 2005099353 | 10/2005 |
| WO | WO 2006008754 | 1/2006 |
| WO | WO 2006124863 | 11/2006 |
| WO | WO 2007002325 | 1/2007 |
| WO | WO 2008030836 | 3/2008 |
| WO | WO 2008124878 | 10/2008 |
| WO | WO 2009045464 | 4/2009 |
| WO | WO 2010/041051 | 4/2010 |
| WO | WO2010065824 A2 | 6/2010 |
| WO | WO 2010065865 | 6/2010 |
| WO | WO 2010072734 | 7/2010 |
| WO | WO 2010077740 | 7/2010 |
| WO | WO 2010083441 | 7/2010 |
| WO | WO2010138582 A2 | 12/2010 |
| WO | WO 2011068560 | 6/2011 |
| WO | WO 2011068561 | 6/2011 |
| WO | WO 2011149492 | 12/2011 |
| WO | WO 2012058392 | 5/2012 |
| WO | WO 2012071374 | 5/2012 |
| WO | WO 2012121758 | 9/2012 |

OTHER PUBLICATIONS

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Tse, C. et al., "ABT-263: A Potent and Orally Bioavailable Bcl-2 Family Inhibitor," Cancer Research, 2008, vol. 68 (9), pp. 3421-3428—Including Supplementary Data.
Bardwell, P.D., et al., 2009, "The Bcl-2 family antagonist ABT-737 significantly inhibits multiple animal models of autoimmunity," J. Immunol 182(12): 7482-9.
Becker D.P., et al., "Azaadamantane Benzamide 5-HT4 Agonists: Gastrointestinal Prokinetic SC-54750" Bioorganic and Medicinal Chemistry Letters, 2004, vol. 14 (22), pp. 5509-5512.
Beylot, M., et al., "In Vivo Studies of Intrahepatic Metabolic Pathways," Diabetes Metabolism, 1997, vol. 23 (3), pp. 251-257.
Blagojevic, N., et al., "Role of heavy water In Boron Neutron Capture Therapy," Topics in Dosimetry & Treatment Planning for Neutron Capture Therapy, 1994, pp. 125-134.
Blake, M. I., et al., "Studies With Deuterated Drugs," Journal of Pharmaceutical Sciences, 1975, vol. 64 (3), pp. 367-391.
Brickner, S.J., et al., "Synthesis and Antibacterial Activity of U-1 00592 and U-100766,Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Bruncko, M., et al., "Studies Leading to Potent, Dual Inhibitors of Bcl-2 and Bcl-XL," Journal of Medicinal Chemistry, 2007, vol. 50 (4), pp. 641-662.
Cancer [online], [retrieved on Jul. 6, 2007]. Retrieved from the internet, <URL: http://www.nlm.nih.gov/medlineplus/cancer.html>.
Cancer [online], [retrieved on Jul. 6, 2007]. Retrieved from the internet, <URL: http://en.wikipedia.org/wiki/Cancer>.
Certo, M., et al., "Mitochondria Primed by Death Signals Determine Cellular Addiction to Antiapoptotic Bcl-2 Family Members," Cancer Cell, 2006, vol. 9 (5), pp. 351-365.
Cross, L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Crowley, M.M., et al., "Pharmaceutical Applications of Hot-melt Extrusion: Part 1," Drug Development and Industrial Pharmacy, 2007, vol. 33 (9), pp. 909-926.
Czajka, D. M., et al., "Effect of Deuterium Oxide on the Reproductive Potential of Mice," Annals of the New York Academy of Sciences, 1960, vol. 84, pp. 770-779.
Czajka, D. M., et al., "Physiological Effects of Deuterium on Dogs," American Journal of Physiology, 1961, vol. 201 (2), pp. 357-362.
Del Gaizo Moore, V., et al., "BCL-2 Dependence and ABT-737 Sensitivity in Acute Lymphoblastic Leukemia," Blood, 2008, vol. 111 (4), pp. 2300-2309.
Durocher, Y., et al., "High-Level and High-Throughput Recombinant Protein Production by Transient Transfection of Suspension-Growing Human 293-EBNA 1 Cells," Nucleic Acids Research, 2002, vol. 30 (2), pp. e9.
Eliel, E. L., et al., "Stereochemistry of Organic Compounds," 1994, pp. 119-120, 1206, John Wiley & Sons, Inc. New York. Table of Contents.
Fairhurst, A.M., et al., "Systemic IFN-Aipha Drives Kidney Nephritis in B6.Sie123 Mice," European Journal of Immunology, 2008, vol. 38 (7), pp. 1948-1960.
U.S. Department of Health and Human Services Food and Drug Administration Center for Drug Evaluation and Research, Guidance for Industry, Aug. 2000, [retrieved on Jan. 25, 2012]. Retrieved from the internet <URL: http://www.fda.gov/downloads/Drugs/GuidanceComplianceRegulatorylnformation/Guidances/ucm070246.pdf.>.
Foster, A. B., et al., "Deuterium Isotope Effects in the Metabolism of Drugs and Xenobiotics: Implications for Drug Design," Advances in Drug Research, 1985, vol. 14, pp. 2-36.
Gelfand, M.C., et al., "Therapeutic Studies in NZB/W Mice II. Relative Efficacy of Azathioprine, Cyclophosphamide and Methylprednisolone," Arthritis and Rheumatism, 1972, vol. 15 (3), pp. 247-252.
Golub, T.R., et al.,"Molecular Classifcation of Cancer: Class Discovery and Class Prediction by Gene Expression Monitoring", Science (1999), vol. 286, pp. 531-537.
Guo, Z., et al., "Relationship between the Expression of bel- 2. Fas/FasL and the Apoptosis of Peripheral Lymphocytes in Patients with Systemic lupus Erythematosus," Chinese Journal of Dermatology, 2001, vol. 34 (1 ), pp. 25 and 27.
Harada, H., et al., "Survival Factor-Induced Extracellular Signal-Regulated Kinase Phosphorylates Bim, Inhibiting Its Association with Bax and Proapoptotic Activity," Proceedings of the National Academy of Sciences, 2004, vol. 101 (43), pp. 15313-15317.
Hoepfner, E.M., et al., eds., "Fiedler Encyclopedia of Excipients for Pharmaceuticals, Cosmetics and Related Areas," 5th Edition, Editio Cantor Verlag Aulendorf, 2002, Table of Contents.
Humerickhouse, R, "Clinical Activity of the Potent and Selective Bcl-2 Inhibitor ABT-199: . . . " Symposium presentation, Apr. 9, 2013, AARC Annual Meeting (Wash. DC), pp. 1-31.
Jones, C. D., et al., "Effects of Substituent Modification on Face Selection in Reduction," Journal of Organic Chemistry, 1998, vol. 63 (8), pp. 2758-2760.
Kato, S., et al., "Synthesis of Deuterated Mosapride Citrate," Journal of Labelled Compounds and Radiopharmaceuticals, 1995, vol. 36 (10), pp. 927-932.
Kayagaki, N., et al., "BAFF/BLyS Receptor 3 Binds the B Cell Survival Factor BAFF Ligand through a Discrete Surface Loop and Promotes Processing of NF-kB2," Immunity, 2002, vol. 10, pp. 515-524.
Klein, C.E., et al., "The Tablet Formulation of Lopinavir/Ritonavir Provides Similar Bioavailability to the Soft-Gelatin Capsule Formulation With Less Pharmacokinetic Variability and Diminished Food Effect," Journal of Acquired Immune Deficiency Syndromes, 2007, vol. 44 (4), pp. 401-410.
Korolkovas, A., "Development of Drugs" in: Essentials of Medicinal Chemistry, Second Edition, John Wiley and Sons, 1988, pp. 53-138.
Kushner, D.J., et al., "Pharmacological uses and perspectives of heavy water and deuterated compounds," Canadian Journal of Physiology and Pharmacology, 1999, vol. 77 (2), pp. 79-88.
Kwok, S.K., et al., "Dysfunctional Interferon-a Production by Peripheral Plasmacytoid Dendritic Cells upon Toll-like Receptor-9

(56) References Cited

OTHER PUBLICATIONS

Stimulation in Patients with Systemic Lupus Erythematosus," Arthritis Research & Therapy, 2008, vol. 10 (2), pp. R29.
Lala, P.K., et al., "Role of nitric oxide in tumor progression: lessons from experimental tumors." Cancer Metastasis Rev. Mar. 1998; vol. 17(1), pp. 91-106.
Laurent, S.A., et al., "Synthesis of "Trioxaquantel" Derivatives as Potential New Antischistosomal Drugs," European Journal of Organic Chemistry, 2008, vol. 5, pp. 895-913.
Leuner, C., et al., "Improving Drug Solubility for Oral Delivery Using Solid Dispersions," European Journal of Pharmaceutics and Biopharmaceutics : Official Journal of Arbeitsgemeinschaft Fur Pharmazeutische Verfahrenstechnik E.V., 2000, vol. 50 (1), pp. 47-60.
Liao, G., "ABT-199 BH-3 Mimetic Enters Phase Ia Trial for Chronic Lymphocytic Leukemia" [Asian Scientist Magazine online], [retrieved on Aug. 12, 2011]. Retrieved from the Internet <URL: http://www.asianscientist.com/tech-pharma/abt-199-bh-3-mimetic-wehi-phase-ia-trial-chronic-lymphocytic-leukemia>.
Liu, K., et al., "What do Mouse Models Teach us about Human SLE?," Clinical Immunology, 2006, vol. 119 (2), pp. 123-130.
Lizondo, J., et al., "Linezolid: Oxazolidinone antibacterial," Drugs of the Future, 1996, vol. 21 (11), pp. 1116-1123.
Mallesham, B., et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Marquina, R., et al , "Inhibition of B Cell Death causes the Development of an IgA Nephropathy in (New Zealand White × C57BL/6)F(1)-bcl-2 Transgenic Mice," Journal of Immunology, 2004, vol. 172 (11), pp. 7177-7185.
Mason, K.D., et al, "Programmed anuclear cell death delimits platelet life span," Cell, 2007, vol. 128 (6), pp. 1173-1186.
Mathian, A., et al., "IFN-a induces Early Lethal Lupus in Preautoimmune (New Zealand Black × New Zealand White) F1 but not in BALB/c Mice," Journal of Immunology, 2005, vol. 174 (5), pp. 2499-2506.
Mizushima, S., et al., "pEF-BOS, a Powerful Mammalian Expression Vector," Nucleic Acids Research, 1990, vol. 18 (17), pp. 5322.
Oltersdorf, T., et al., "An inhibitor of Bcl-2 family proteins induces regression of solid tumours," Nature, 2005, 435: 677-681.
Park, C.M., et al., "Discovery of an Orally Bioavailable Small Molecule Inhibitor of Prosurvival B-Cell Lymphoma 2 Proteins," Journal of Medicinal Chemistry, 2008, vol. 51 (21 ), pp. 6902-6915.
Ramos, M.A., et al., "Modulation of Autoantibody Production by Mycophenolate Mofetil: Effects on the Development of SLE in (NZB × NZW)F1 Mice," Nephrology Dialysis Transplantation, 2003, vol. 18 (5), pp. 878-883.
Roberti, M., et al., "Synthesis and Biological Evaluation of Resveratrol and Analogues as Apoptosis-lnducing Agents," J. Med. Chem. 2003, 46, 3546-3554.
Sharma, D.K, et al., "Solubility Enhancement Strategies for Poorly Water-Soluble Drugs in Solid Dispersions: A Review," Asian Journal of Pharmecutics, 2007, vol. 1(1), pp. 9-19.
Skoug, J.W., et al. Enabling Discovery Through Formulation. American Association of Pharmaceutical Scientists (AAPS) Webinar [online] Presented Mar. 18, 2010, 12:30 PM to 2:00PM EDT.
Souers, A.J., et al., "ABT-199, a potent and selective BCL-2 inhibitor, achieves antitumor activity while sparing platelets," Nature Medicine, 2013, 19: 202-208.
Sperling, L.H., "Introduction to Physical Polymer Science," 2nd Edition, John Wiley & Sons, Inc., 1992, Table of Contents.
Thomson, J.F., "Physiological Effects of D20 in Mammals," Annals of the New York Academy of Sciences, 1960, vol. 84, pp. 736-744.
Vandenberg, C.J. and Cory, S., "ABT-199, a new Bcl-2-specific BH3 mimetic, . . . " Blood, Prepublished online Jan. 22, 2013; doi:10.1182/blood-2013-01-475855.
Wang, Z.X., "An Exact Mathematical Expression for Describing Competitive Binding of Two Different Ligands to a Protein Molecule," FEBS Letters, 1995, vol. 360 (2), pp. 111-114.
Wendt, M.D., "Discovery of ABT-263, a Bel-Family Protein Inhibitor: Observations on Targeting a Large Protein-Protein Interaction," Expert Opinion on Drug Discovery, 2008, vol. 3 (9), pp. 1123-1143.
Wilson, L.E., et al., "Autoimmune Disease Complicating Antivrial Therapy for Hepatitis C Virus Infection," Seminars in Arthritis and Rheumatism, 2002, vol. 32(3), pp. 163-173.
Xie, M., et al., "Apoptosis and Fas/bc1-2 Expression in Peripheral Blood Lymphocytes of Patients with Systemic Lupus Erythematosus," Chinese Medical Journal, 1999, vol. 113, pp. 1072.
Zhang, H., et al., "Bc1-2 Family Proteins are Essential for Platelets Survival," Cell Death and Differentiation, 2007, vol. 14 (5), pp. 943-951.
Zhang, R., et al., "Effect of Interferon-Alpha in Systemic Lupus Erthematosus (SLE) Serum on the Differentiation and Maturation of Dendritic Cells derived from CD34+ Hematopoietic Precursor Cells," Journal of Nanjing Medical University, 2009, vol. 23 (6), pp. 380-385.
International Searching Authority, Supplementary International Search Report mailed Feb. 24, 2011 for Application No. PCT/US2009/066722, 2 pages.
International Searching Authority, Supplementary International Search Report mailed Mar. 24, 2011 for Application No. PCT/US2009/066790, 2 pages.
International Searching Authority, Supplementary International Search Report mailed Sep. 8, 2011 for PCT/US2010/036198, 2 pages.
International Searching Authority, Supplementary International Search Report mailed Jun. 28, 2012 for Application No. PCT/US2010/057587, 2 pages.
International Searching Authority, International Search Report mailed Aug. 4, 2010 for Application No. PCT/US2009/066722, 4 pages.
International Searching Authority, International Search Report mailed Jul. 28, 2010 for Application No. PCT/US2009/066790, 4 pages.
International Searching Authority, International Search Report mailed Jul. 28, 2010 for Application No. PCT/US2009/067335, 4 pages.
International Searching Authority, International Search Report mailed Jun. 17, 2010 for Application No. PCT/EP2009/067689, 4 pages.
International Searching Authority, International Search Report mailed Feb. 9, 2011 for Application No. PCT/US2010/036198, 3 pages.
International Searching Authority, International Search Report mailed Aug. 16, 2010 for Application No. PCT/US2010/036844, 3 pages.
International Searching Authority, International Search Report for Application No. For PCT/US2010/036919, mailed Aug. 19, 2010, 3 pages.
International Searching Authority, International Search Report for Application No. PCT/US2010/057587, mailed Apr. 28, 2011, 2 pages.
International Searching Authority, International Search Report for Application No. PCT/US2011/058024, mailed Jan. 27, 2012, 3 pages.
International Searching Authority, International Search Report for Application No. PCT/US2011/061769, mailed Feb. 14, 2012, 3 pages.
International Searching Authority, International Search Report for Application No. PCT/US2011/054959, mailed Dec. 16, 2011, 3 pages.
International Searching Authority, Written Opinion for Application No. PCT/US2007/077579, mailed Mar. 10, 2009, 9 pages.
International Searching Authority, Written Opinion for Application No. PCT/US2009/066722, mailed Jun. 7, 2011, 7 pages.
International Searching Authority, Written Opinion for Application No. PCT/US2010/036198 mailed Nov. 29, 2011, 7 pages.
International Searching Authority, Written Opinion for Application No. PCT/US2010/036844, mailed Jun. 5, 2012, 8 pages.
International Searching Authority, Written Opinion for Application No. PCT/US2010/036919, mailed Jun. 5, 2012, 7 pages.
Gupta, P. K., "Solutions and Phase Equilibria", in Remington, The Science and Practice of Pharmacy, 21$^{st}$ Edition, 2005, 211-230.
Vasanthavada, M. et al., "Development of Solid Dispersion of Poorly Water-Soluble Drugs", in Water-Insoluble Drug Formulation, Liu, R., ed., 2$^{nd}$ Edition, 2008, 499-529.
International Search Authority, International Search Report, PCT/US2011/061678, Feb. 3, 2012.

SALTS AND CRYSTALLINE FORMS OF AN APOPTOSIS-INDUCING AGENT

CROSS-REFERENCE TO RELATED APPLICATIONS

This application claims the benefit of provisional application Ser. No. 61/416,656, filed Nov. 23, 2010, which is hereby incorporated by reference as if set forth in its entirety.

Cross-reference is also made, without claim to benefit of priority or admission as to prior art status, to the following pending U.S. application containing subject matter related to the present application: Ser. No. 12/787,682 (published as U.S. 2010/0305122) titled "Apoptosis-inducing Agents for the Treatment of Cancer and Immune and Autoimmune Diseases," the entire disclosure of which is incorporated herein by reference.

FIELD OF THE INVENTION

The present invention relates to salts and crystalline forms of an apoptosis-inducing agent, to pharmaceutical dosage forms comprising such salts and crystalline forms, to processes for preparing salts and crystalline forms, and to methods of use thereof for treating diseases characterized by overexpression of anti-apoptotic Bcl-2 family proteins.

BACKGROUND OF THE INVENTION

Overexpression of Bcl-2 proteins correlates with resistance to chemotherapy, clinical outcome, disease progression, overall prognosis or a combination thereof in various cancers and disorders of the immune system.

Evasion of apoptosis is a hallmark of cancer (Hanahan & Weinberg (2000) *Cell* 100:57-70). Cancer cells must overcome a continual bombardment by cellular stresses such as DNA damage, oncogene activation, aberrant cell cycle progression and harsh microenvironments that would cause normal cells to undergo apoptosis. One of the primary means by which cancer cells evade apoptosis is by up-regulation of anti-apoptotic proteins of the Bcl-2 family.

A particular type of neoplastic disease for which improved therapies are needed is non-Hodgkin's lymphoma (NHL). NHL is the sixth most prevalent type of new cancer in the U.S. and occurs primarily in patients 60-70 years of age. NHL is not a single disease but a family of related diseases, which are classified on the basis of several characteristics including clinical attributes and histology.

One method of classification places different histological subtypes into two major categories based on natural history of the disease, i.e., whether the disease is indolent or aggressive. In general, indolent subtypes grow slowly and are generally incurable, whereas aggressive subtypes grow rapidly and are potentially curable. Follicular lymphomas are the most common indolent subtype, and diffuse large-cell lymphomas constitute the most common aggressive subtype. The oncoprotein Bcl-2 was originally described in non-Hodgkin's B-cell lymphoma.

Treatment of follicular lymphoma typically consists of biologically-based or combination chemotherapy. Combination therapy with rituximab, cyclophosphamide, doxorubicin, vincristine and prednisone (R-CHOP) is routinely used, as is combination therapy with rituximab, cyclophosphamide, vincristine and prednisone (RCVP). Single-agent therapy with rituximab (targeting CD20, a phosphoprotein uniformly expressed on the surface of B-cells) or fludarabine is also used. Addition of rituximab to chemotherapy regimens can provide improved response rate and increased progression-free survival.

Radioimmunotherapy agents, high-dose chemotherapy and stem cell transplants can be used to treat refractory or relapsed NHL. Currently, there is not an approved treatment regimen that produces a cure, and current guidelines recommend that patients be treated in the context of a clinical trial, even in a first-line setting.

First-line treatment of patients with aggressive large B-cell lymphoma typically consists of rituximab, cyclophosphamide, doxorubicin, vincristine and prednisone (R-CHOP), or dose-adjusted etoposide, prednisone, vincristine, cyclophosphamide, doxorubicin and rituximab (DA-EPOCH-R).

Most lymphomas respond initially to any one of these therapies, but tumors typically recur and eventually become refractory. As the number of regimens patients receive increases, the more chemotherapy-resistant the disease becomes. Average response to first-line therapy is approximately 75%, 60% to second-line, 50% to third-line, and about 35-40% to fourth-line therapy. Response rates approaching 20% with a single agent in a multiple relapsed setting are considered positive and warrant further study.

Other neoplastic diseases for which improved therapies are needed include leukemias such as chronic lymphocytic leukemia (like NHL, a B-cell lymphoma) and acute lymphocytic leukemia.

Chronic lymphoid leukemia (CLL) is the most common type of leukemia. CLL is primarily a disease of adults, more than 75% of people newly diagnosed being over the age of 50, but in rare cases it is also found in children. Combination chemotherapies are the prevalent treatment, for example fludarabine with cyclophosphamide and/or rituximab, or more complex combinations such as CHOP or R-CHOP.

Acute lymphocytic leukemia, also known as acute lymphoblastic leukemia (ALL), is primarily a childhood disease, once with essentially zero survival but now with up to 75% survival due to combination chemotherapies similar to those mentioned above. New therapies are still needed to provide further improvement in survival rates.

Current chemotherapeutic agents elicit their antitumor response by inducing apoptosis through a variety of mechanisms. However, many tumors ultimately become resistant to these agents. Bcl-2 and Bcl-$X_L$ have been shown to confer chemotherapy resistance in short-term survival assays in vitro and, more recently, in vivo. This suggests that if improved therapies aimed at suppressing the function of Bcl-2 and Bcl-$X_L$ can be developed, such chemotherapy-resistance could be successfully overcome.

Involvement of Bcl-2 proteins in bladder cancer, brain cancer, breast cancer, bone marrow cancer, cervical cancer, CLL, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer and the like is described in International Patent Publication Nos. WO 2005/024636 and WO 2005/049593.

Involvement of Bcl-2 proteins in immune and autoimmune diseases is described, for example, by Puck & Zhu (2003) *Current Allergy and Asthma Reports* 3:378-384; Shimazaki et al. (2000) *British Journal of Haematology* 110(3):584-590; Rengan et al. (2000) *Blood* 95(4):1283-1292; and Holzelova et al. (2004) *New England Journal of Medicine* 351(14): 1409-1418. Involvement of Bcl-2 proteins in bone marrow transplant rejection is disclosed in United States Patent Application Publication No. US 2008/0182845.

Compounds that occupy a binding site on Bcl-2 proteins are known. To be therapeutically useful by oral administration, such compounds desirably have high binding affinity, exhibiting for example $K_i$<1 nM, preferably <0.1 nM, more preferably <0.01 nM, to proteins of the Bcl-2 family, specifically Bcl-2, Bcl-$X_L$ and Bcl-w. It is further desirable that they be formulated in a manner that provides high systemic exposure after oral administration. A typical measure of systemic exposure after oral administration of a compound is the area under the curve (AUC) resulting from graphing plasma concentration of the compound versus time from oral administration.

Apoptosis-inducing drugs that target Bcl-2 family proteins such as Bcl-2 and Bcl-$X_L$ are best administered according to a regimen that provides continual, for example daily, replenishment of the plasma concentration, to maintain the concentration in a therapeutically effective range. This can be achieved by daily parenteral, e.g., intravenous (i.v.) or intraperitoneal (i.p.) administration. However, daily parenteral administration is often not practical in a clinical setting, particularly for outpatients. To enhance clinical utility of an apoptosis-inducing agent, for example as a chemotherapeutic in cancer patients, a dosage form with acceptable oral bioavailability would be highly desirable. Such a dosage form, and a regimen for oral administration thereof, would represent an important advance in treatment of many types of cancer, including NHL, CLL and ALL, and would more readily enable combination therapies with other chemotherapeutics.

Different crystalline forms of an apoptosis-inducing agent can provide different properties with respect to stability, solubility, dissolution rate, hardness, compressibility and melting point, among other physical and mechanical properties. Because ease of manufacture, formulation, storage and transport of an apoptosis-inducing agent is dependent on at least some of these properties, there is a need in the chemical and therapeutic arts for identification of new salts and crystalline forms of apoptosis-inducing agents and ways for reproducibly generating such salts and crystalline forms.

SUMMARY OF THE INVENTION

The present disclosure relates to salts and crystalline forms of an apoptosis-inducing agent, referred to herein as "Compound 1," which has the systematic name 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, and which can be depicted by the formula:

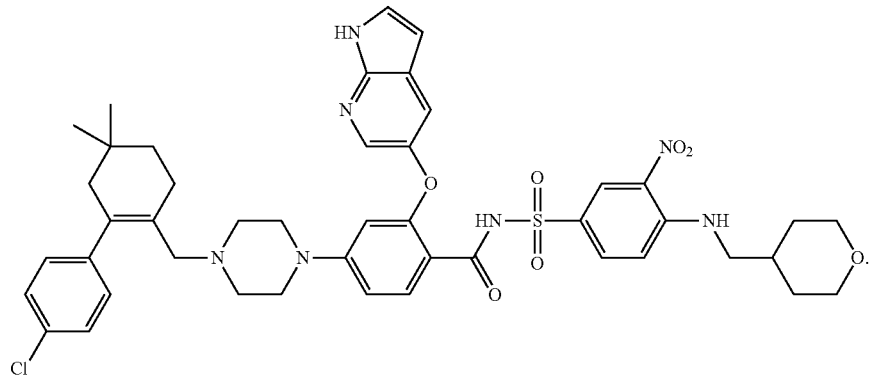 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Following synthesis of Compound 1, as described herein, the product may be recovered as a powder in an amorphous state. An amorphous form of Compound 1 may not be well suited for use as an active pharmaceutical ingredient (API) for various types of downstream formulations. More particularly, an amorphous form of Compound 1 can be difficult and therefore expensive to purify and can present process control problems.

The present disclosure provides a series of novel salts and crystalline forms of Compound 1 suitable for use as API in a wide variety of formulation types, including those where the API is present in particulate form together with excipients, for example in orally deliverable tablets or capsules. The salts and crystalline forms of Compound 1 may also be useful where the crystalline form is converted to a non-crystalline form (e.g., solution or amorphous form) when formulated. Also included are ways to prepare the salts and crystalline forms of Compound 1. Salt and crystalline forms of Compound 1 can be used to modulate and/or improve the physicochemical properties of the API, including solid state properties (e.g., crystallinity, hygroscopicity, melting point, hydration potential, polymorphism, etc.), pharmaceutical properties (e.g., solubility/dissolution rate, stability, compatibility, etc.), and crystallization characteristics (e.g., purity, yield, morphology, etc.), as non-limiting examples.

In some embodiments, the salt or crystalline form of Compound 1 includes those of Compound 1 free base anhydrate having PXRD pattern A, Compound 1 free base anhydrate having PXRD pattern B, Compound 1 free base hydrate having PXRD pattern C, Compound 1 free base hydrate having PXRD pattern D, Compound 1 free base dichloromethane solvate having pattern E, Compound 1 free base ethyl acetate solvate having PXRD pattern F, Compound 1 free base ethyl acetate solvate having PXRD pattern G, Compound 1 free base acetonitrile solvate having PXRD pattern H, Compound 1 free base acetonitrile solvate having PXRD pattern I, Compound 1 free base acetone solvate having PXRD pattern J, Compound 1 hydrochloride having PXRD pattern K, Compound 1 hydrochloride hydrate having PXRD pattern L, Compound 1 sulfate having PXRD pattern M, and Compound 1 free base tetrahydrofuran (THF) solvate having PXRD pattern N, each having the respective powder X-ray diffraction patterns as described herein.

In some embodiments, the crystalline forms of Compound 1 free base dichloromethane solvate, Compound 1 free base acetonitrile solvate, Compound 1 hydrochloride, and Compound 1 free base tetrahydrofuran solvate have the respective crystal lattice parameters as described herein.

In another embodiment, Compound 1 hydrochloride is provided.

In another embodiment, Compound 1 sulfate is provided.

In some embodiments, an API composition is provided comprising Compound 1 as the API, in which at least a portion, for example at least about 10%, of the Compound 1 in the composition is in a salt or crystalline form. In some embodiments, greater than 95% or essentially 100% of the API in such a composition is a salt or crystalline form of Compound 1.

In some embodiments, a pharmaceutical composition is provided that comprises a salt or crystalline form of Compound 1 as described herein and one or more pharmaceutically acceptable excipients.

In some embodiments, a process for preparing a pharmaceutical solution composition of Compound 1 is provided, where the process comprises dissolving a salt or crystalline form of Compound 1 as described herein with a pharmaceutically acceptable solvent or mixture of solvents.

In some embodiments, a method for treating a disease characterized by apoptotic dysfunction and/or overexpression of an anti-apoptotic Bcl-2 family protein is provided, where the method comprises administering to a subject having the disease a therapeutically effective amount of (a) a salt or crystalline form of Compound 1 as described herein or (b) a pharmaceutical composition comprising a salt or crystalline form of Compound 1 as described herein and one or more pharmaceutically acceptable excipients.

In some embodiments, a method for treating a disease characterized by apoptotic dysfunction and/or overexpression of an anti-apoptotic Bcl-2 family protein is provided, where the method comprises preparing a solution or dispersion of a salt or crystalline form of Compound 1 described herein in a pharmaceutically acceptable solvent or mixture of solvents, and administering the resulting solution or dispersion in a therapeutically effective amount to a subject having the disease.

Additional embodiments of the invention, including particular aspects of those provided above, will be found in, or will be evident from, the detailed description that follows.

DETAILED DESCRIPTION

Figure 1:
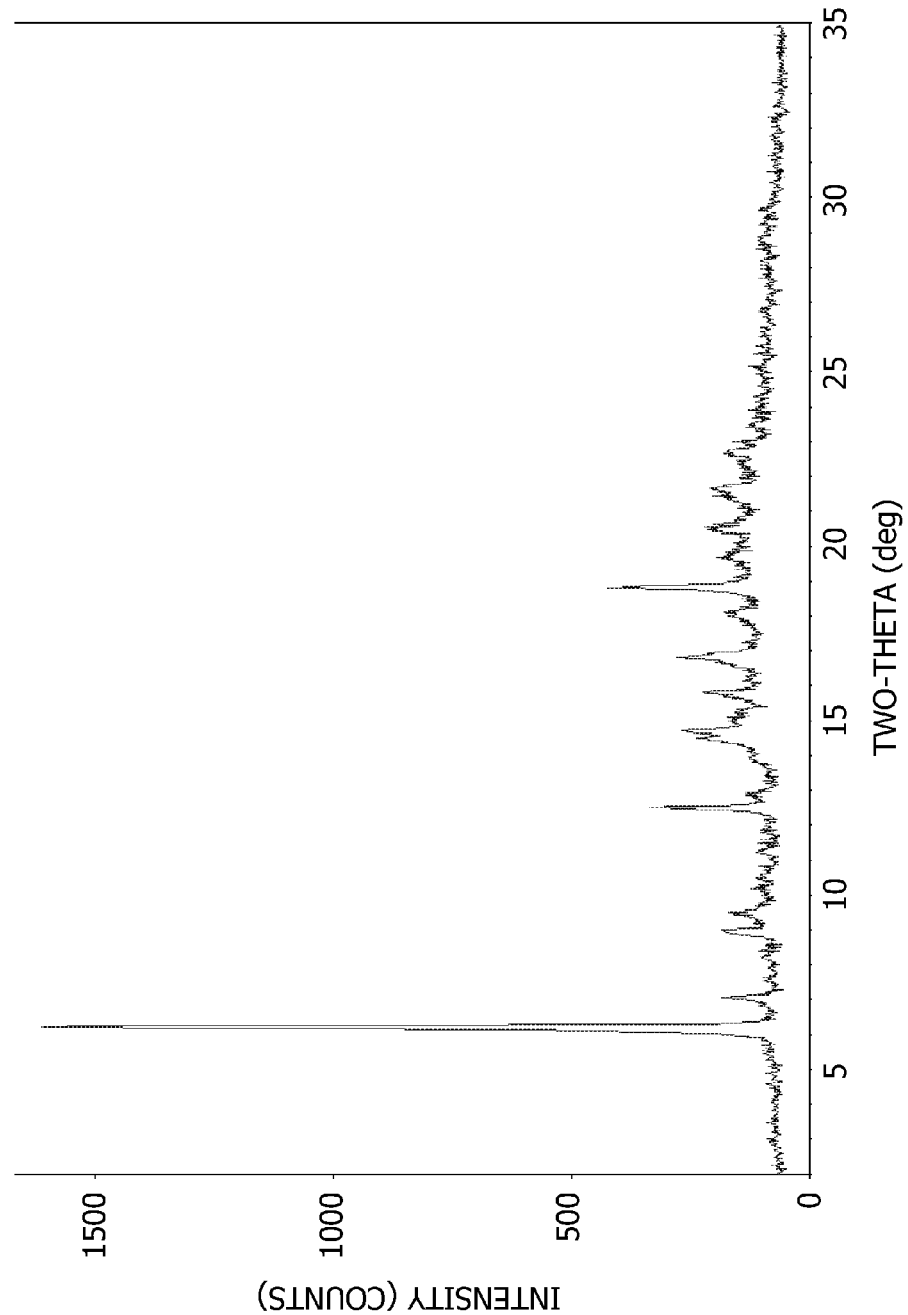
FIG. 1 is a PXRD scan of Compound 1 anhydrate designated pattern A.

The term "free base" is used for convenience herein to refer to Compound 1 parent compound as distinct from any salt thereof, while recognizing that the parent compound, strictly speaking, is zwitterionic at neutral conditions and thus does not always behave as a true base.

An apoptosis-inducing agent, referred to herein as Compound 1, has the systematic name 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, and can be depicted by the formula:

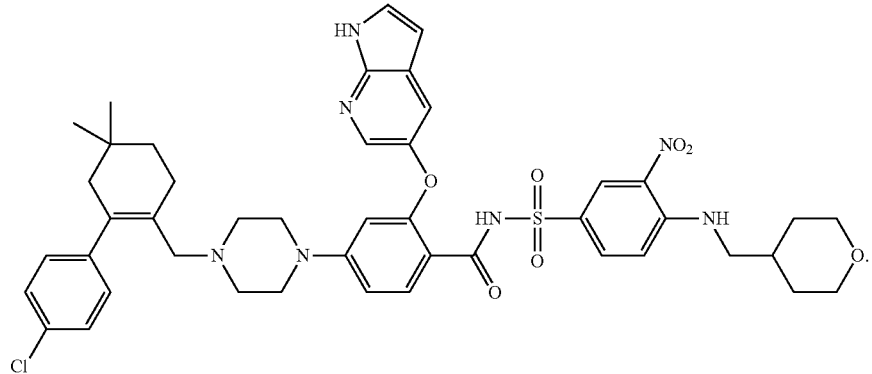 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In various embodiments, salts and crystalline forms of Compound 1 are provided. Crystalline forms include solvates, hydrates, anhydrates, and salts of Compound 1.

In contrast to an amorphous form of Compound 1 free base and an amorphous form of a Compound 1 salt, a crystalline form is characterized by the presence of observable peaks in a powder x-ray diffraction (PXRD) pattern measured on the crystalline form. For crystalline forms prepared to yield suitably sized single-crystals, the crystalline form can be further characterized through an experimental determination of the unit cell parameters, the identification of the crystallographic space group to which a single crystal belongs, or both of these. Once the unit cell parameters are known, the location of the diffraction peaks, and in particular the 2θ values of the peaks in a PXRD pattern can be calculated, to further characterize the crystalline form. Of course, the PXRD pattern can also be measured experimentally for such crystalline forms. If not only the cell parameters but a three dimensional single crystal structure is known, then not only the positions but also the intensity of the peaks in the diffraction pattern can be calculated in further characterization of the crystalline form.

The PXRD patterns measured or calculated for the salts and crystalline forms reported herein represent a fingerprint that can be compared to other experimentally determined patterns to find a match. Identity of the respective crystalline forms is established by overlap or match of an experimentally determined PXRD pattern with the PXRD pattern of the crystalline forms reported herein. In various embodiments, the salts and crystalline forms are characterized by exhibiting at least one of the PXRD peaks reported here. Thus, in various embodiments, a salt or crystalline form is characterized by a match of two or more peaks, a match of 3 or more peaks, 4 or more peaks, or 5 or more peaks, and so on, from the respective PXRD patterns.

An embodiment of the synthesis of Compound 1 (free base) and representative intermediate compounds is presented below. The exemplified compounds are named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates are named using ChemDraw® Ver. 9.0.5 (CambridgeSoft, Cambridge, Mass.).

Synthesis of Compound 1

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound A 3-nitro-4-((tetrahydro-2H-pyran-4-yl)methylamino)benzenesulfonamide A mixture of 4-fluoro-3-nitrobenzenesulfonamide (2.18 g), 1-(tetrahydropyran-4-yl)methylamine (1.14 g), and triethylamine (1 g) in tetrahydrofuran (30 mL) were stirred overnight, neutralized with concentrated HCl and concentrated. The residue was suspended in ethyl acetate and the precipitates were collected, washed with water and dried to provide the title compound.

Compound B methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The reaction mixture was warmed to room temperature and stirred for 24 hours. The organic layer was washed with brine, dried ($Na_2SO_4$), filtered, and concentrated to give the product.

Compound C methyl 2-(4-chlorophenyl)-4,4-dimethylcyclohex-1-enecarboxylate

Compound B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product.

Compound D (2-(4-chlorophenyl)-4,4-dimethylcyclohex-1-enyl)methanol

To a mixture of $LiBH_4$ (13 g), Compound C (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The extracts were dried ($Na_2SO_4$), filtered, and concentrated. The crude product was chromatographed on silica gel with 0-30% ethyl acetate/hexanes.

Compound E tert-butyl 4-((2-(4-chlorophenyl)-4,4-dimethylcyclohex-1-enyl)methyl)piperazine-1-carboxylate Mesyl Chloride (7.5 mL) was added via syringe to Compound D (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Compound F 1-((2-(4-chlorophenyl)-4,4-dimethylcyclohex-1-enyl)methyl)piperazine

Compound E (200 mg) and triethylsilane (1 mL) were stirred in dichloromethane (15 mL) and trifluoroacetic acid (15 mL) for 1 hour. The mixture was concentrated, taken up in ethyl acetate, washed twice with $NaH_2PO_4$, and brine, and dried ($Na_2SO_4$), filtered and concentrated.

Compound G 5-bromo-1-(triisopropylsilyl-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried (Na$_2$SO$_4$), filtered, and concentrated. The crude product was chromatographed on silica gel with 10% ethyl acetate/hexanes.

Compound H 1-(triisopropylsilyl)-1H-pyrrolo[2,3-b]pyridin-5-ol

To a mixture of Compound G (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M NaOH (69 mL) was added, followed by 30% H$_2$O$_2$ (8.43 mL), and the solution was stirred for 1 hour. Na$_2$S$_2$O$_3$ (10 g) was added, and the pH was adjusted to 4-5 with concentrated HCl and solid NaH$_2$PO$_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes.

Compound I methyl 2-(1H-pyrrolo[2,3-b]pyridin-5-yloxy)-4-fluorobenzoate

A mixture of Compound H (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Compound J methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound I (1.55 g), Compound F (2.42 g), and HK$_2$PO$_4$ (1.42 g) in dimethylsulfoxide (20 mL) at 135° C. was stirred for 24 hours. The reaction was cooled, diluted with ether (400 mL), and washed with 3× 1M NaOH, and brine, and concentrated. The crude product was chromatographed on silica gel with 10-50% ethyl acetate/hexanes.

Compound K 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid Compound J (200 mg) in dioxane (10 mL) and 1M NaOH (6 mL) at 50° C. was stirred for 24 hours. The reaction was cooled, added to NaH$_2$PO$_4$ solution, and extracted three times with ethyl acetate. The combined extracts were washed with brine, and concentrated to give the pure product.

Compound L

Compound 1 Free Base 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound K (3.39 g), Compound A (1.87 g), 1-ethyl-3-[3-(dimethylamino)propyl]-carbodiimide hydrochloride (2.39 g), and 4-dimethylaminopyridine (1.09 g) were stirred in CH$_2$Cl$_2$ (40 mL) for 24 hours. The reaction was cooled and chromatographed on silica gel with 25-100% ethyl acetate/hexanes, then 10% methanol/ethyl acetate with 1% acetic acid, to give the product (1.62 g, 32%) as a solid. $^1$H NMR (300 MHz, dimethylsulfoxide-d$_6$) 11.65 (br s, 1H), 8.55 (br s, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 1H), 3.84 (m, 1H), 3.30 (m, 4H), 3.07 (m, 4H), 2.73 (m, 2H), 2.18 (m, 6H), 1.95 (m, 2H), 1.61 (dd, 2H), 1.38 (m, 2H), 1.24 (m, 4H), 0.92 (s, 6H).

Preparation of Compound 1 free base is also described in Example 5 of U.S. application Ser. No. 12/787,682 (published as U.S. 2010/0305122) titled "Apoptosis-inducing agents for the treatment of cancer and immune and autoimmune diseases," the entire disclosure of which is incorporated herein by reference. A solid can be prepared from the chromatography eluate; for example, by using freeze-drying, precipitation, or rotary evaporation techniques. The product of this process can be a solid that is amorphous in character.

Salts and crystal forms of Compound 1 have been prepared as described in the following examples.

Compound 1 Free Base Anhydrate

PXRD Pattern A

The following two routes can prepare this crystalline form, where drying at ambient conditions involves leaving the solid material at room temperature and exposed to air overnight. For example, solvent can be allowed to evaporate.

Example 1

Compound 1 free base dichloromethane solvate having pattern E (see below) was dried at ambient conditions.

Example 2

Compound 1 free base ethyl acetate solvate having pattern F (see below) was dried at ambient conditions.

Powder X-ray diffraction pattern and peak listing are shown in FIG. 1 and Table 1, respectively.

TABLE 1

| Peak Listing for Compound 1 Free Base Anhydrate Pattern A Peak Position (° 2θ) |
|---|
| 6.3 |
| 7.1 |
| 9.0 |
| 9.5 |
| 12.5 |
| 14.5 |
| 14.7 |

TABLE 1-continued

Peak Listing for Compound 1 Free Base Anhydrate Pattern A
Peak Position (° 2θ)

| |
|---|
| 15.9 |
| 16.9 |
| 18.9 |

Compound 1 Free Base Anhydrate

PXRD Pattern B

Example 3

Compound 1 free base acetonitrile solvate pattern H was dried at ambient conditions.

Figure 2:
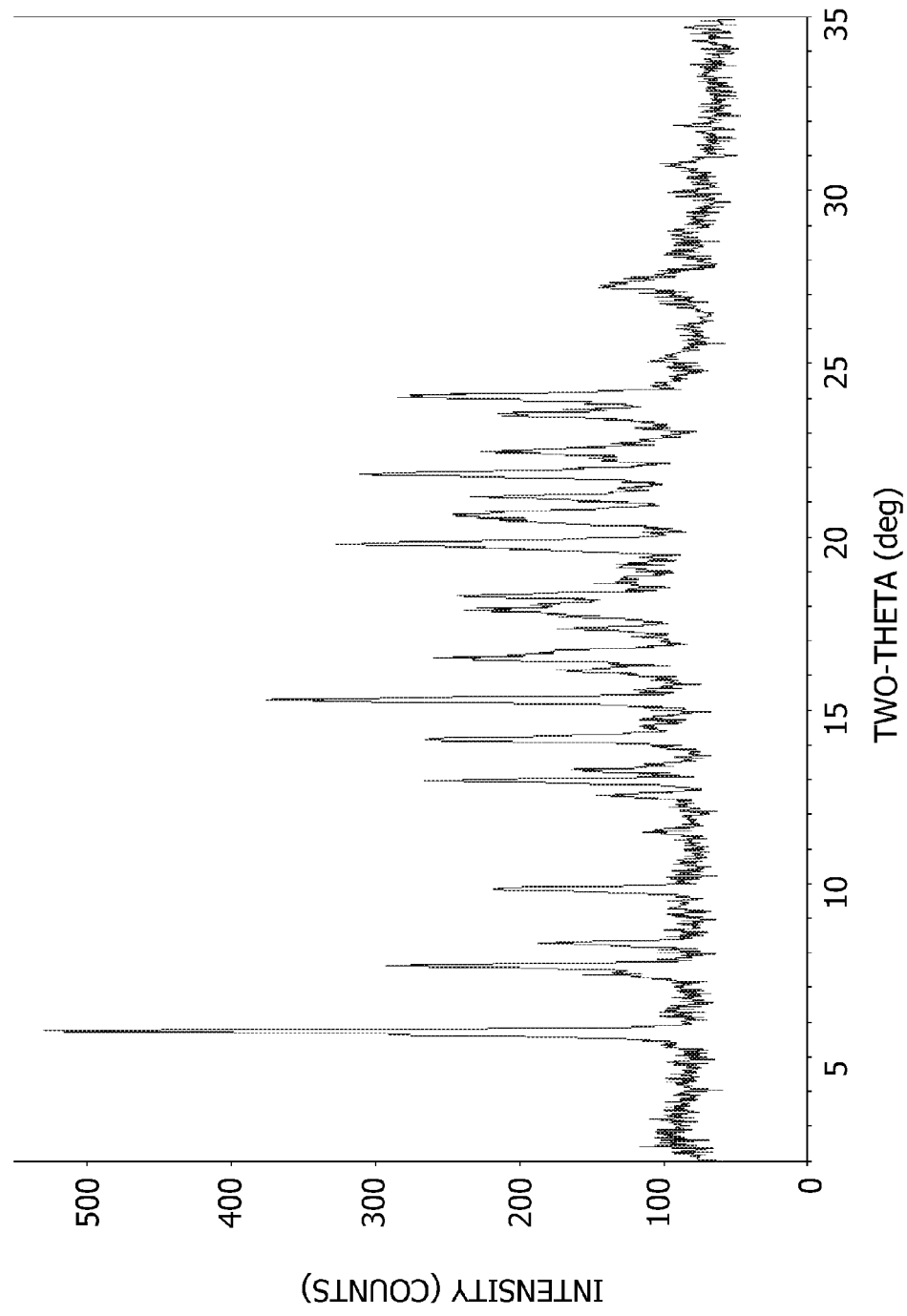
FIG. 2 is a PXRD scan of Compound 1 anhydrate designated pattern B.

Powder X-ray diffraction pattern and peak listing are shown in FIG. 2 and Table 2, respectively.

TABLE 2

Peak Listing for Compound 1 Free Base Anhydrate Pattern B
Peak Position (° 2θ)

| |
|---|
| 5.8 |
| 7.7 |
| 8.3 |
| 9.9 |
| 13.0 |
| 13.3 |
| 14.2 |
| 15.3 |
| 16.6 |
| 17.9 |
| 18.3 |
| 19.8 |
| 20.7 |
| 21.2 |
| 21.9 |
| 22.5 |
| 23.6 |
| 24.1 |

Compound 1 Free Base Hydrate

PXRD Pattern C

The free base hydrate, characterized by Pattern C, can be prepared in three ways.

Example 4

Compound 1 free base methanol solvate was dried at ambient conditions.

Example 5

Compound 1 Free Base Ethanol Solvate was Dried at Ambient Conditions.

Example 6

Compound 1 free base 2-propanol solvate was dried at ambient Conditions.

Figure 3:
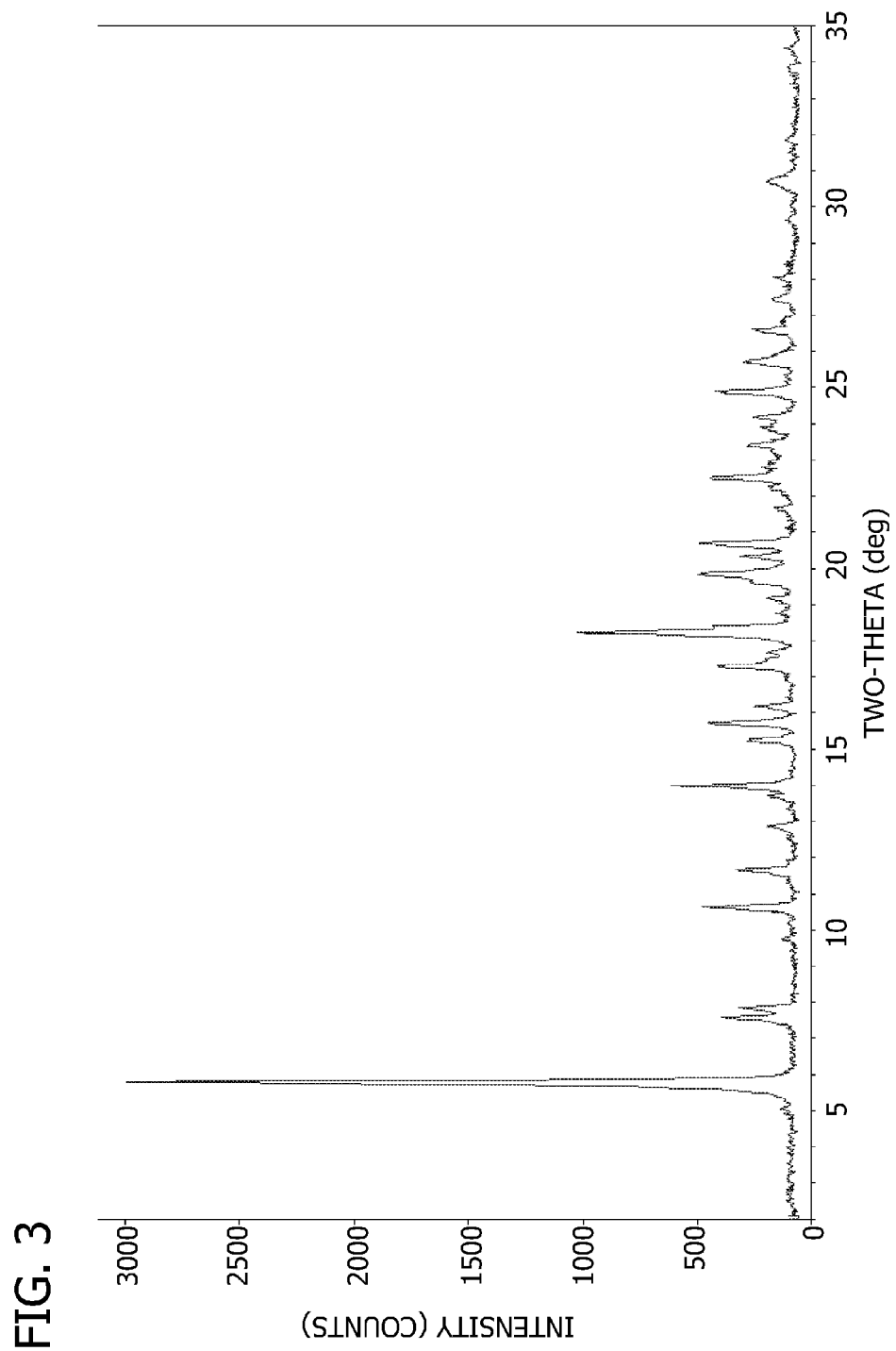
FIG. 3 is a PXRD scan of Compound 1 hydrate designated pattern C.

Powder X-ray diffraction pattern and peak listing are shown in FIG. 3 and Table 3, respectively.

TABLE 3

Peak Listing for Compound 1 Free Base Hydrate Pattern C
Peak Position (° 2θ)

| |
|---|
| 5.8 |
| 7.6 |
| 7.9 |
| 10.7 |
| 11.7 |
| 14.0 |
| 15.3 |
| 15.8 |
| 17.4 |
| 18.3 |
| 19.9 |
| 20.4 |
| 20.7 |
| 22.5 |
| 24.9 |
| 25.8 |
| 26.7 |

Compound 1 Free Base Hydrate

PXRD Pattern D

Example 7

Compound 1 Free Base Ethyl Acetate Solvate Pattern G was Dried at Ambient Conditions.

Figure 4:
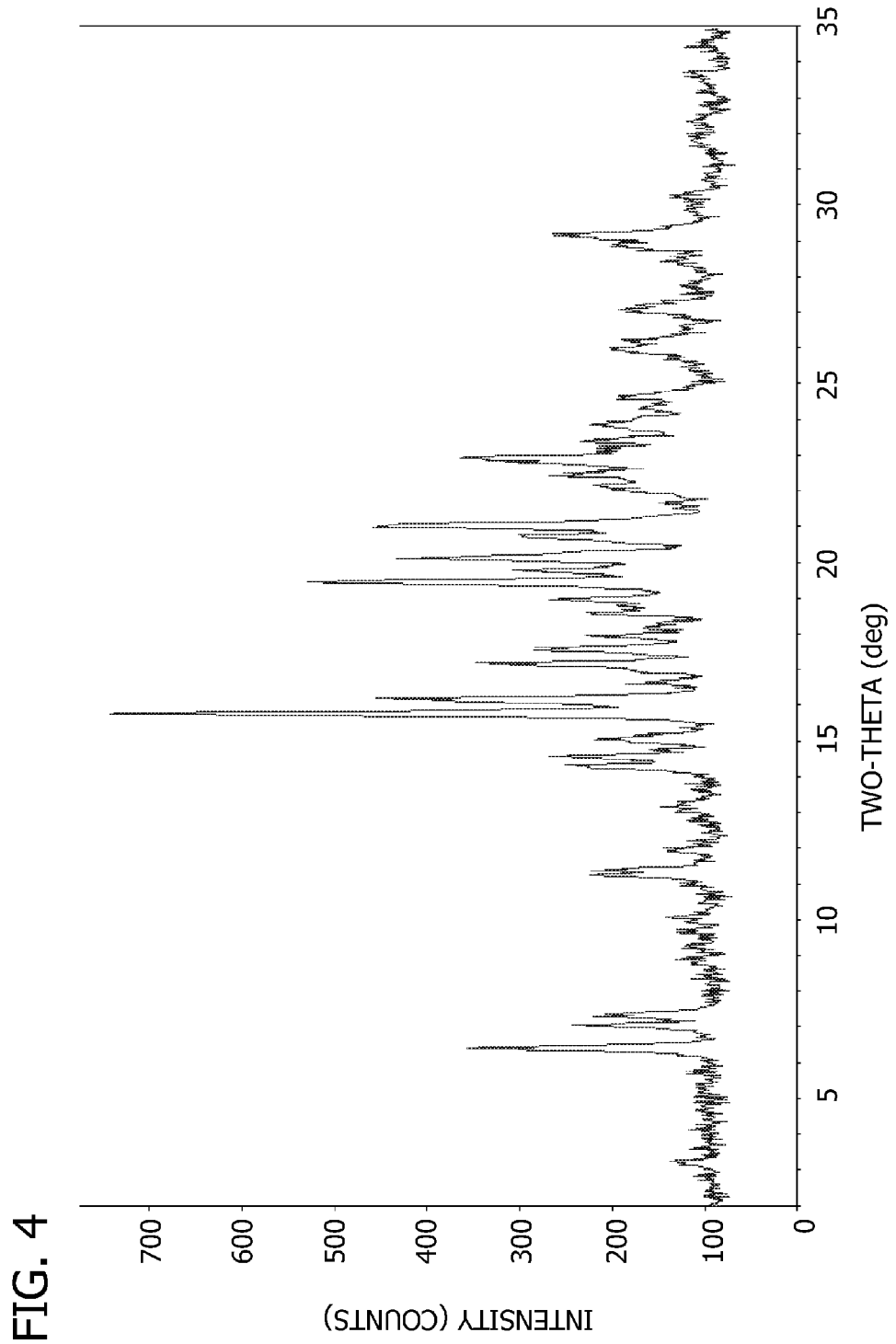
FIG. 4 is a PXRD scan of Compound 1 hydrate designated pattern D.

Powder X-ray diffraction pattern and peak listing are shown in FIG. 4 and Table 4, respectively.

TABLE 4

Peak Listing for Compound 1 Free Base Hydrate Pattern D
Peak Position (° 2θ)

| |
|---|
| 3.3 |
| 6.4 |
| 7.1 |
| 7.3 |
| 10.1 |
| 11.4 |
| 13.2 |
| 14.4 |
| 14.6 |
| 15.1 |
| 15.8 |
| 16.2 |
| 17.2 |
| 17.6 |
| 18.0 |
| 18.6 |
| 19.0 |
| 19.5 |
| 19.8 |
| 20.2 |
| 20.7 |
| 21.0 |
| 22.5 |
| 23.0 |
| 26.0 |
| 28.9 |
| 29.2 |

Compound 1 Free Base Dichloromethane Solvate

PXRD Pattern E

Example 8

Compound 1 free base solid was suspended in dichloromethane at ambient temperatures to reach its solubility. After equilibrating, the solids were isolated at ambient temperature.

Figure 5:
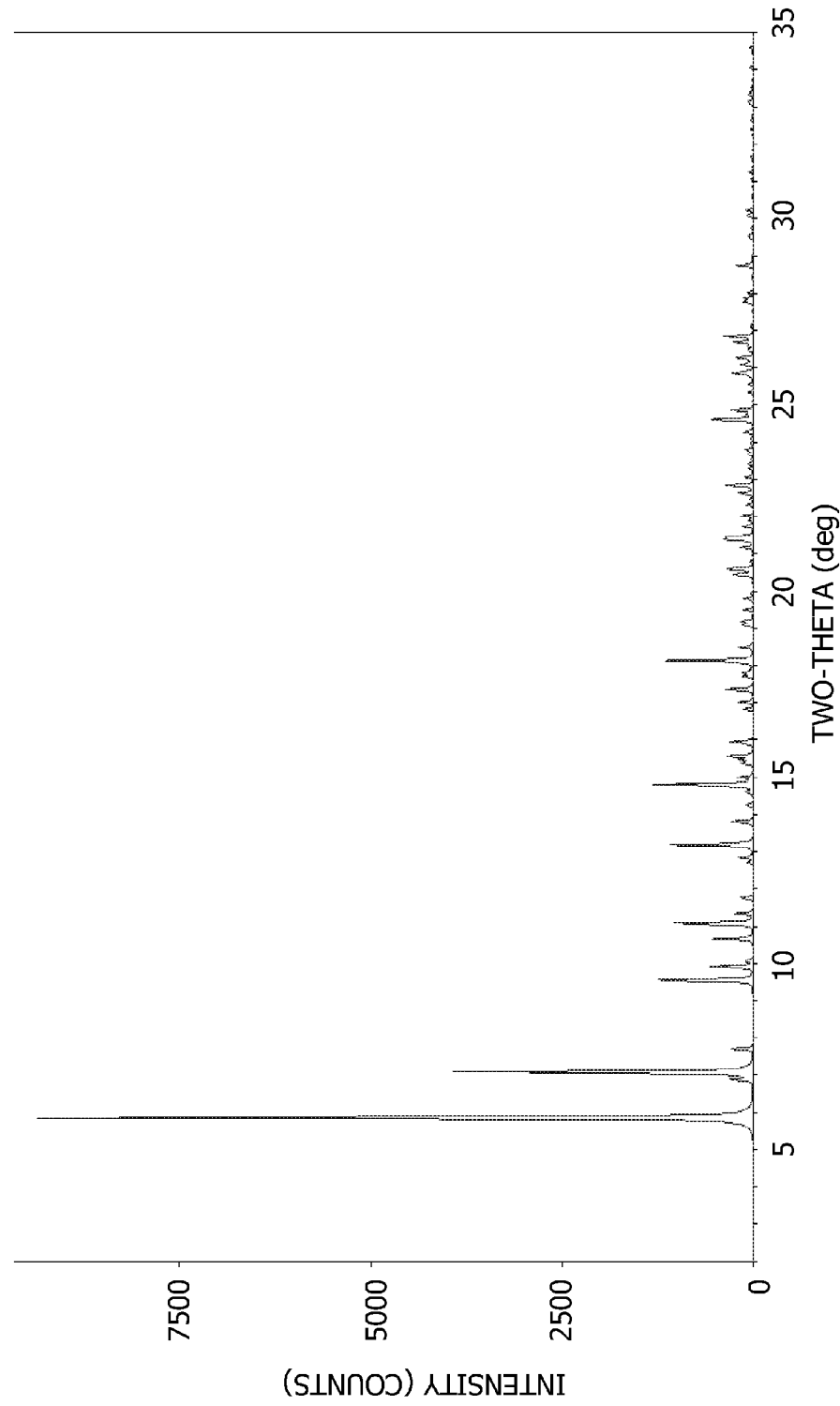
FIG. 5 is a calculated PXRD pattern of Compound 1 dichloromethane solvate designated pattern E.

Powder X-ray diffraction pattern and peak listing are shown in FIG. 5 and Table 5A, respectively. Crystallographic information is listed in Table 5B.

TABLE 5A

Calculated PXRD Peak Listing for Compound 1 Free Base Dichloromethane Solvate Pattern E
Peak Position (° 2θ)

| |
|---|
| 5.9 |
| 7.1 |
| 9.6 |
| 10.0 |
| 10.7 |
| 11.1 |
| 13.2 |
| 14.8 |
| 18.2 |

TABLE 5B

Structural Information for Compound 1 Free Base Dichloromethane Solvate Single Crystal

| Crystal Form | Compound 1 Free Base Dichloromethane Solvate |
|---|---|
| Lattice Type | Monoclinic |
| Space Group | P21/n |
| a (Å) | 13.873 |
| b (Å) | 12.349 |
| c (Å) | 29.996 |
| α (°) | 90.00 |
| β (°) | 92.259 |
| γ (°) | 90.00 |
| Volume (Å$^3$) | 5134.85 |
| Z | 4 |

Compound 1 Free Base Ethyl Acetate Solvate (PXRD Pattern F)

Example 9

Compound 1 free base solid was suspended in ethyl acetate at ambient temperatures to reach its solubility. After equilibrating, the solids were isolated at ambient temperature.

Figure 6:
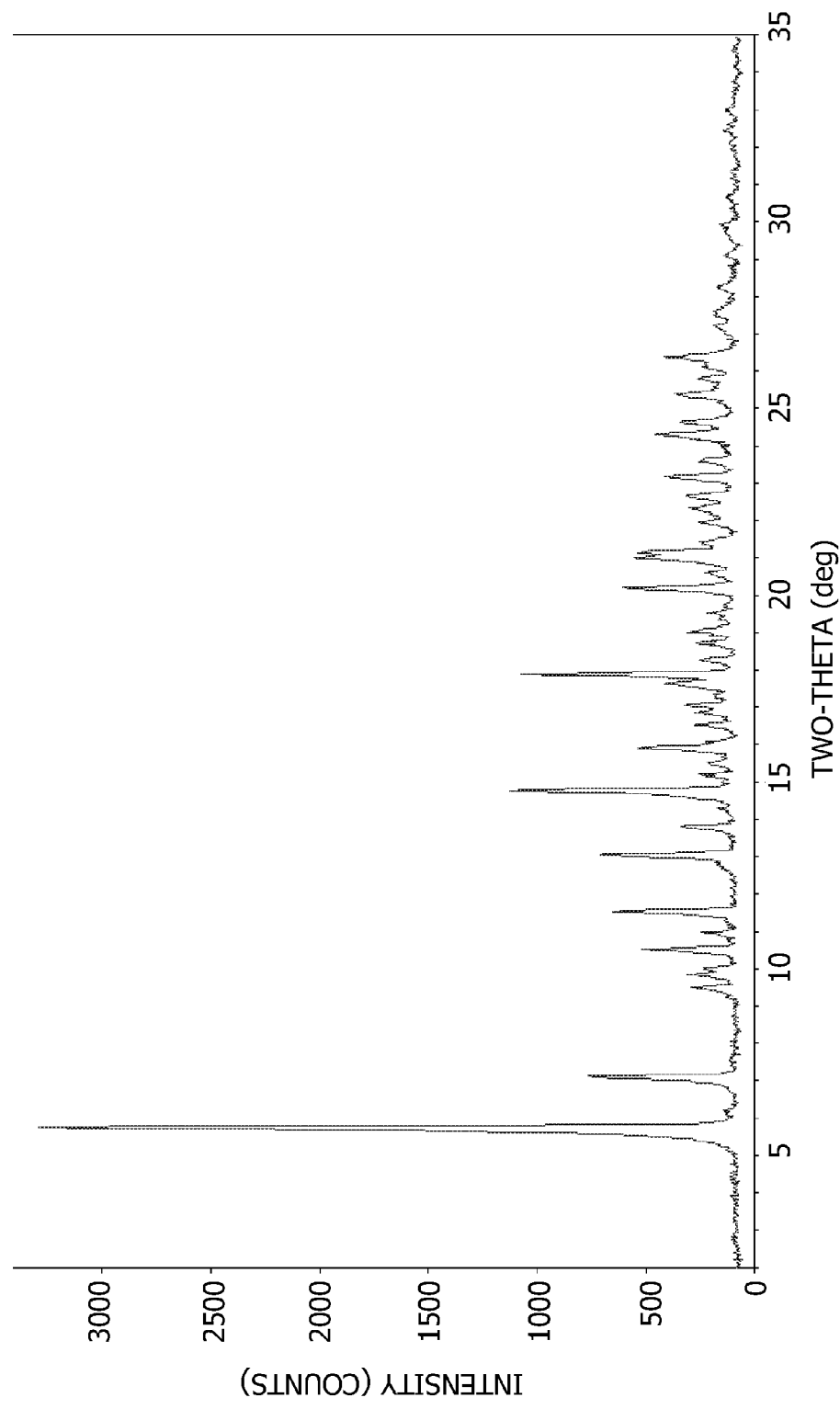
FIG. 6 is a PXRD scan of Compound 1 ethyl acetate solvate designated pattern F.

Powder X-ray diffraction pattern and peak listing are shown in FIG. 6 and Table 6, respectively.

TABLE 6

PXRD Peak Listing for Compound 1 Free Base Ethyl Acetate Solvate Pattern F
Peak Position (° 2θ)

| |
|---|
| 5.8 |
| 7.1 |
| 9.5 |
| 9.9 |
| 10.6 |
| 11.6 |

TABLE 6-continued

PXRD Peak Listing for Compound 1 Free Base Ethyl Acetate Solvate Pattern F
Peak Position (° 2θ)

| |
|---|
| 13.1 |
| 13.8 |
| 14.8 |
| 16.0 |
| 17.9 |
| 20.2 |
| 21.2 |
| 23.2 |
| 24.4 |
| 26.4 |

Compound 1 Free Base Ethyl Acetate Solvate (PXRD Pattern G)

Example 10

Compound 1 free base solid was suspended in ethyl acetate saturated with water at ambient temperatures to reach its solubility. After equilibrating, the solids were isolated at ambient temperature.

Figure 7:
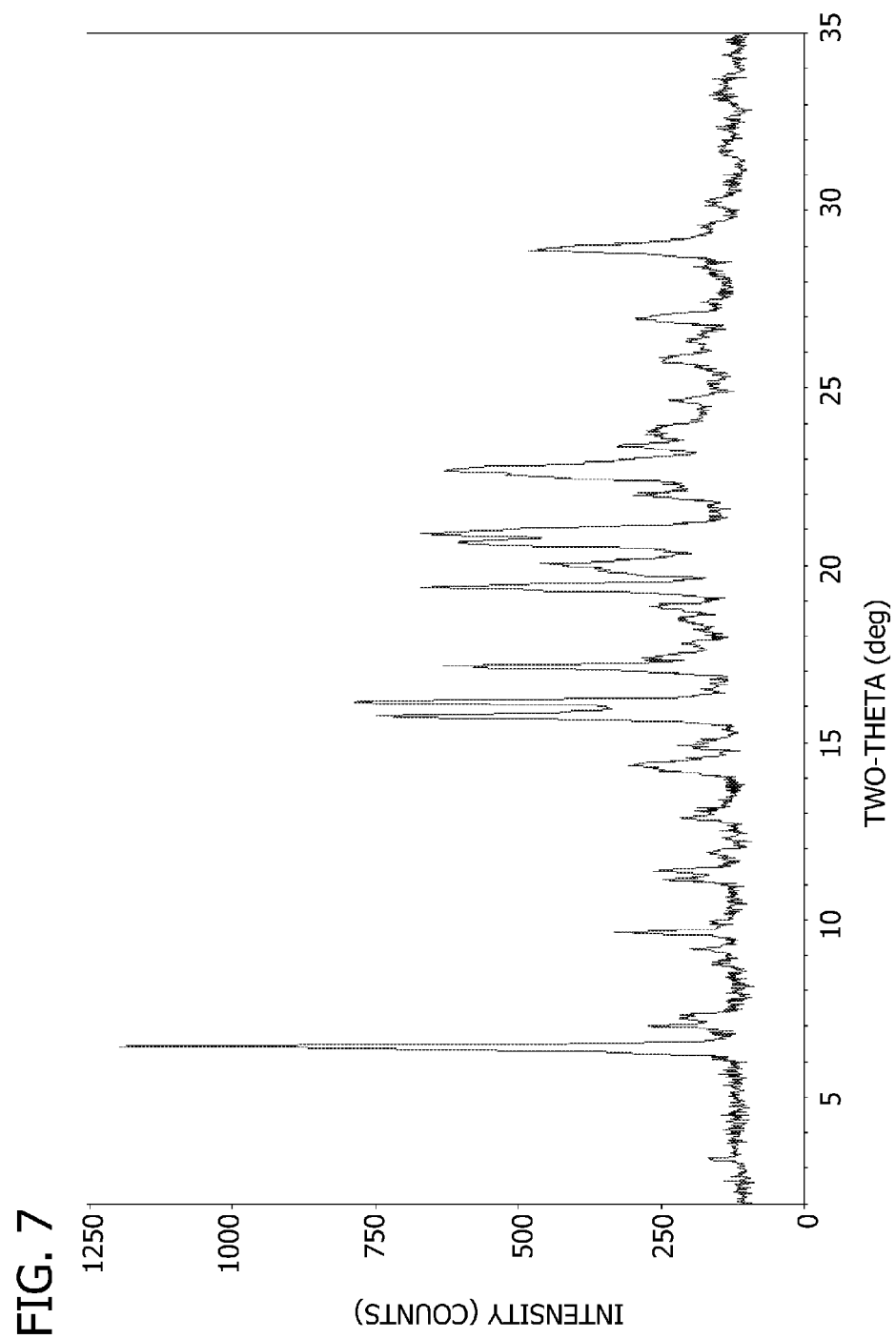
FIG. 7 is a PXRD scan of Compound 1 ethyl acetate solvate designated pattern G.

Powder X-ray diffraction pattern and peak listing shown in FIG. 7 and Table 7, respectively.

TABLE 7

PXRD Peak Listing for Compound 1 Free Base Ethyl Acetate Solvate Pattern G
Peak Position (° 2θ)

| |
|---|
| 3.3 |
| 6.5 |
| 7.0 |
| 7.3 |
| 9.2 |
| 9.7 |
| 11.2 |
| 11.4 |
| 11.9 |
| 12.9 |
| 14.4 |
| 14.9 |
| 15.8 |
| 16.2 |
| 17.2 |
| 17.4 |
| 17.8 |
| 18.5 |
| 18.9 |
| 19.4 |
| 20.1 |
| 20.7 |
| 20.9 |
| 22.0 |
| 22.7 |
| 23.4 |
| 23.8 |
| 24.7 |
| 25.9 |
| 27.0 |
| 28.9 |

Compound 1 Free Base Acetonitrile Solvate

PXRD Pattern H

Example 11

Compound 1 free base solid was suspended in acetonitrile at ambient temperatures to reach its solubility. After equilibrating, the solids were isolated at ambient temperature.

Figure 8:
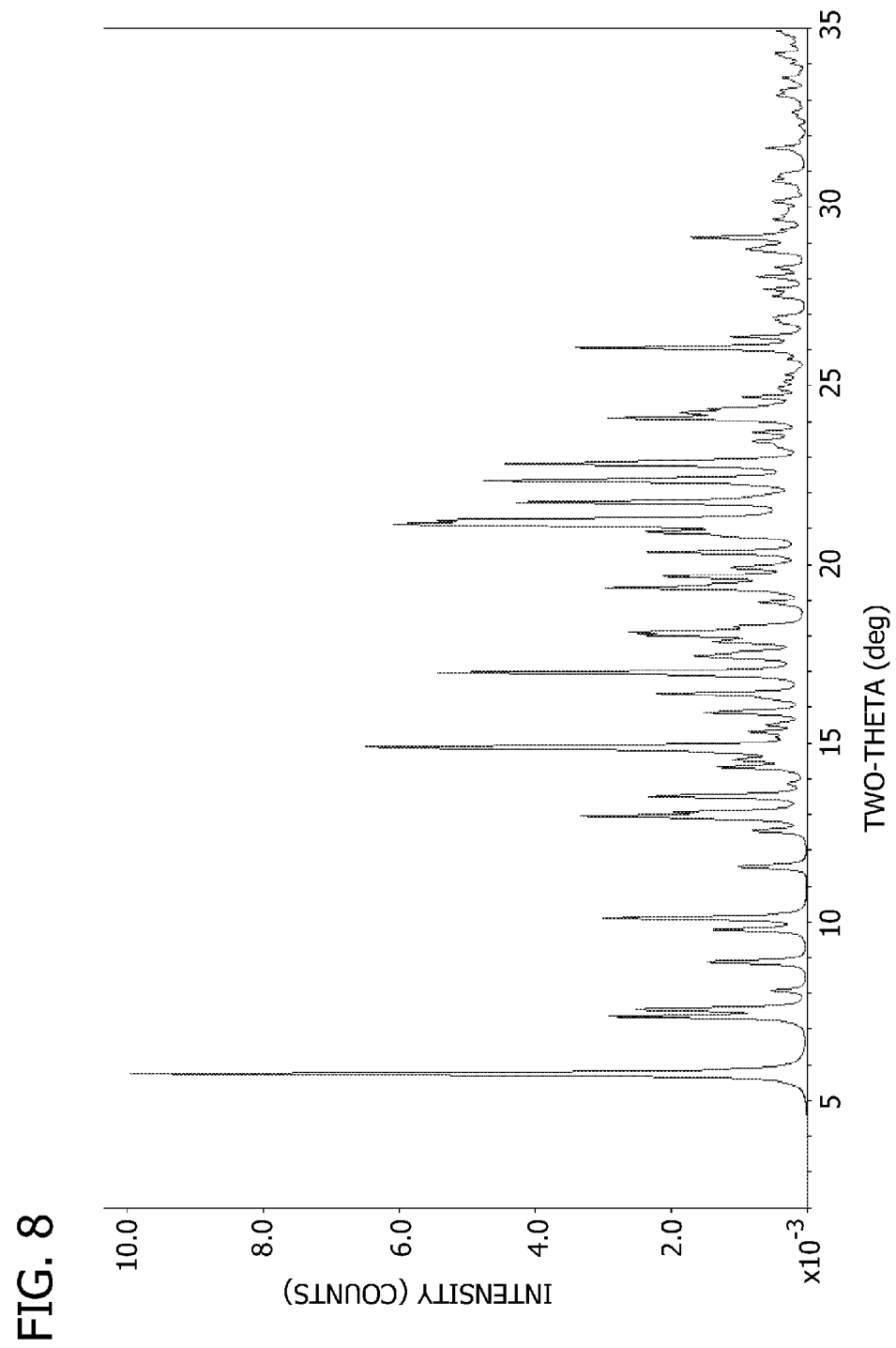
FIG. 8 is a calculated PXRD pattern of Compound 1 acetonitrile solvate designated pattern H.

Powder X-ray diffraction pattern and peak listing are shown in FIG. 8 and Table 8A, respectively. Crystallographic information is listed in Table 8B.

TABLE 8A

Calculated PXRD Peak Listing for Compound 1
Free Base Acetonitrile Solvate Pattern H
Peak Position (° 2θ)

| |
|---|
| 5.8 |
| 7.4 |
| 7.6 |
| 10.2 |
| 13.0 |
| 13.6 |
| 14.9 |
| 16.4 |
| 17.0 |
| 17.5 |
| 18.2 |
| 19.4 |
| 19.7 |
| 20.4 |
| 21.0 |
| 21.2 |
| 21.8 |
| 22.4 |
| 22.9 |
| 24.2 |
| 24.3 |
| 26.1 |
| 29.2 |

TABLE 8B

Structural information for Compound 1 Free
Base Acetonitrile Solvate H Single Crystal

| Crystal Form | Compound 1 Free Base Acetonitrile Solvate A |
|---|---|
| Lattice Type | Triclinic |
| Space Group | P1 |
| a (Å) | 12.836 |
| b (Å) | 13.144 |
| c (Å) | 15.411 |
| α (°) | 92.746 |
| β (°) | 95.941 |
| γ (°) | 113.833 |
| Volume (Å³) | 2354.06 |
| Z | 2 |

Compound 1 Free Base Acetonitrile Solvate (PXRD Pattern I)

Example 12

To a solution of 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid (16 g, 28 mmol) and 3-nitro-4-((tetrahydro-2H-pyran-4-yl)methylamino) benzenesulfonamide (8.83 g, 28 mmol) in DCM (300 mL) was added EDCI (10.74 g, 56 mmol) and DMAP (6.85 g, 56 mmol). The mixture was stirred at r.t. overnight. LC/MS showed the expected product as a single peak. The mixture was diluted with DCM (500 ml) and washed with aq. NaHCO$_3$, water, brine and dried over Na2SO4. The residue after evaporation of solvent was dissolved in DCM and loaded on a column and eluted with 30% ethyl acetate in DCM followed by 1 to 2% MeOH in DCM to give 24.5 g pure product (95% purity) which was dissolved in DMSO and MeOH (1:1) and TFA (2 eq) and loaded on a 330 g C18 column (6 g a time) to give 13.5 g pure (>99.7% purity) product (55% yield). The API was extracted using dichloromethane and then, the solvent was removed using rotary evaporator. The resulting solid was suspended in acetonitrile at ambient temperatures to reach its solubility. After equilibrating, the solids were isolated at ambient temperature.

Figure 9:
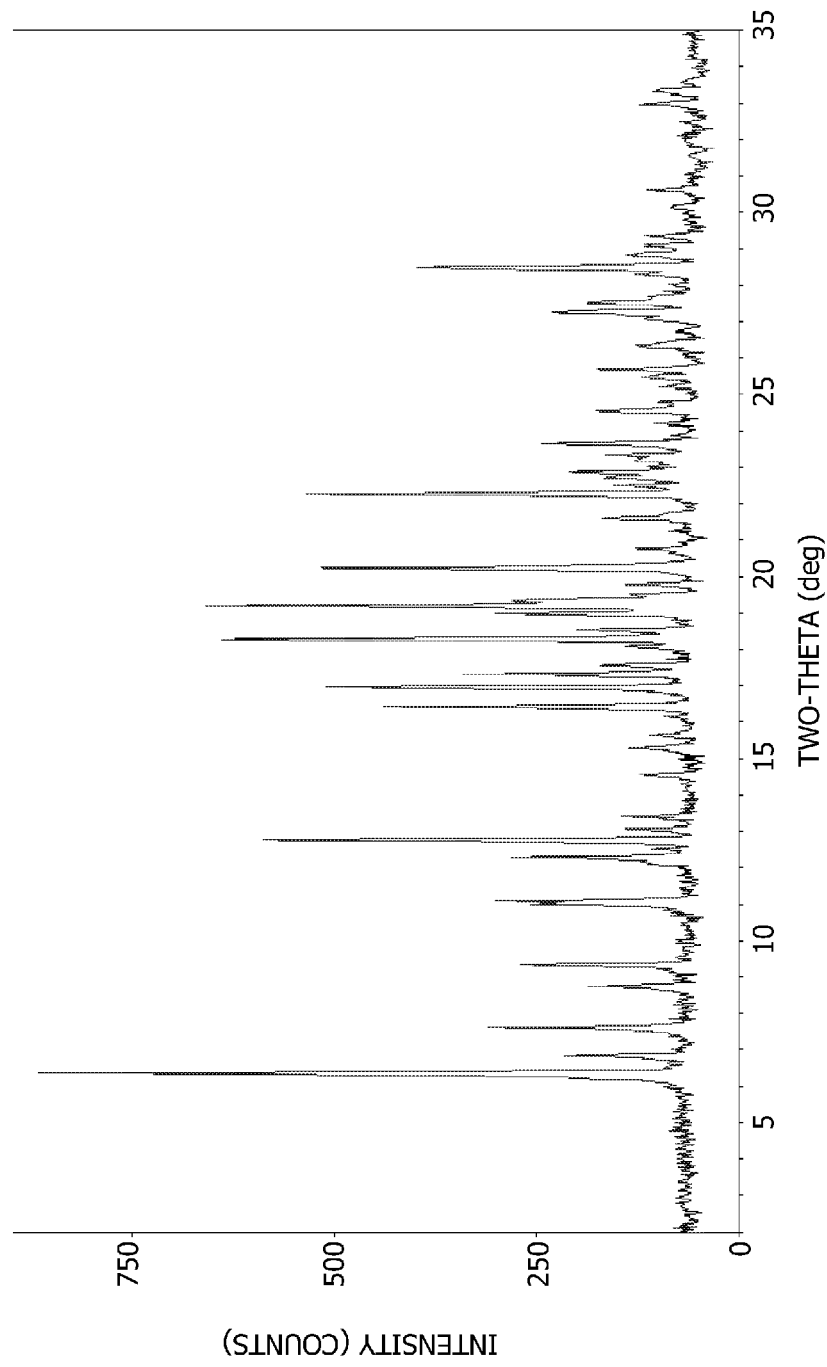
FIG. 9 is a PXRD scan of Compound 1 acetonitrile solvate designated pattern I.

Powder X-ray diffraction pattern and peak listing are shown in FIG. 9 and Table 9, respectively.

TABLE 9

PXRD Peak Listing for Compound 1 Free
Base Acetonitrile Solvate Pattern I
Peak Position (° 2θ)

| |
|---|
| 6.4 |
| 6.9 |
| 7.7 |
| 8.8 |
| 9.4 |
| 11.1 |
| 12.3 |
| 12.8 |
| 16.5 |
| 17.0 |
| 17.4 |
| 18.3 |
| 18.6 |
| 19.0 |
| 19.2 |
| 20.3 |
| 21.6 |
| 22.3 |
| 22.9 |
| 23.7 |

Compound 1 Free Base Acetone Solvate

PXRD Pattern J

Example 13

Compound 1 free base solid was suspended in acetone at ambient temperatures to reach its solubility. After equilibrating, the solids were isolated at ambient temperature.

Figure 10:
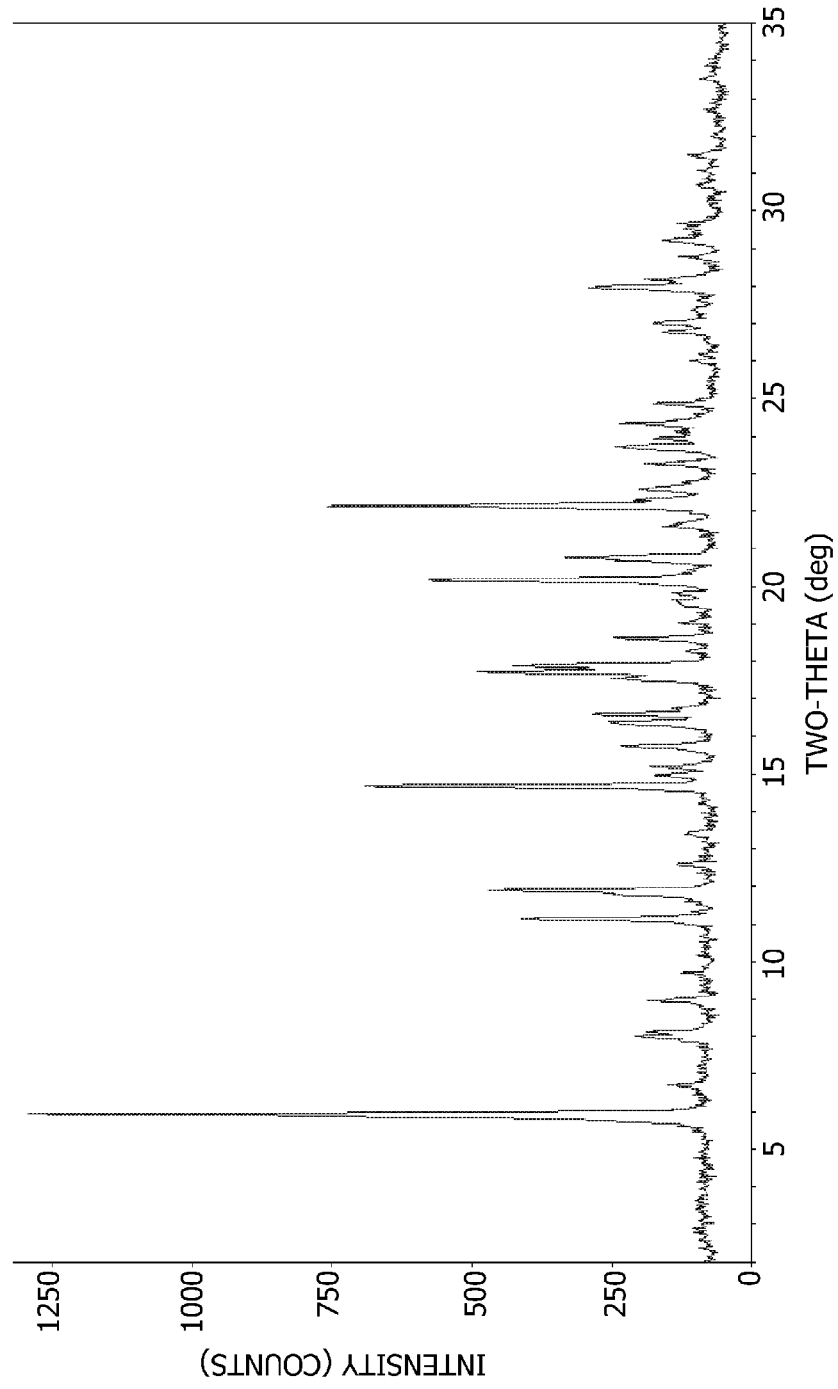
FIG. 10 is a PXRD scan of Compound 1 acetone solvate designated pattern J.

Powder X-ray diffraction pattern and peak listing are shown in FIG. 10 and Table 10, respectively.

TABLE 10

PXRD Peak Listing for Compound 1 Free Base Acetone Solvate Pattern J
Peak Position (° 2θ)

| |
|---|
| 6.0 |
| 6.8 |
| 8.0 |
| 9.0 |
| 9.7 |
| 11.2 |
| 11.9 |
| 12.6 |
| 14.7 |
| 15.0 |
| 15.2 |
| 15.8 |
| 16.4 |
| 16.6 |
| 17.6 |
| 17.8 |
| 17.9 |
| 18.7 |
| 20.2 |
| 20.8 |
| 21.6 |
| 22.2 |
| 22.6 |

TABLE 10-continued

PXRD Peak Listing for Compound 1 Free Base Acetone Solvate Pattern J Peak Position (° 2θ)

| |
|---|
| 23.3 |
| 23.8 |
| 24.0 |
| 24.4 |
| 26.8 |
| 27.1 |
| 28.0 |
| 28.2 |

Compound 1 Hydrochloride

PXRD Pattern K

Example 14

Compound 1 free base solid (16 mg, 0.018 mmol) was suspended in 0.5 mL of acetonitrile. Hydrochloric acid (1M, 25 µL) was added to the suspension while stirring (molar ratio of Compound 1:acid=1:1.4). Compound 1 quickly reacted with hydrochloric acid and formed a clear solution. Yellowish solids, which later crystallized from the solution, were confirmed to be Compound 1 hydrochloride in a 1:1 stoichiometric ratio of free base to HCl.

Figure 11:
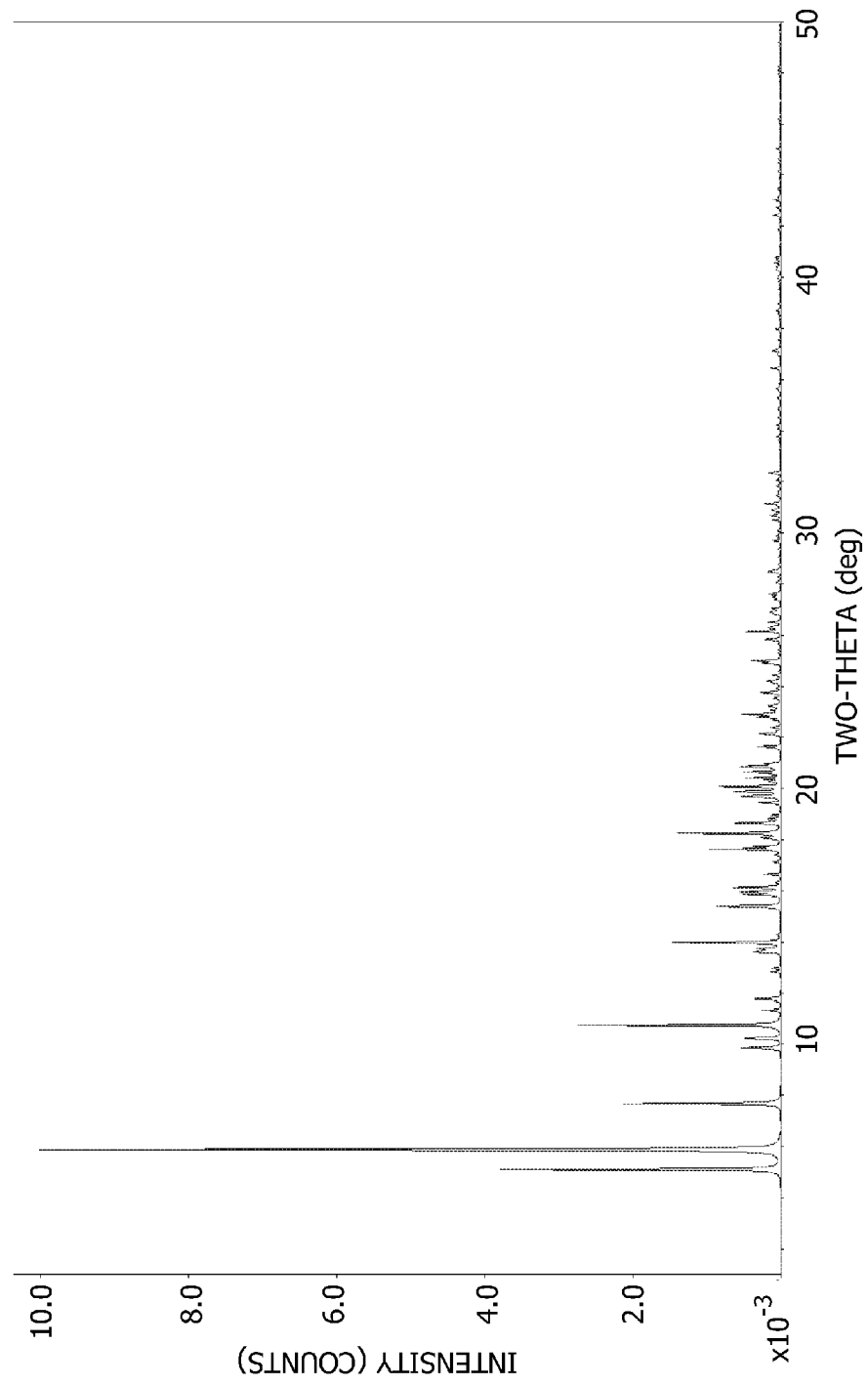
FIG. 11 is a calculated PXRD pattern of Compound 1 hydrochloride designated pattern K.

Powder X-ray diffraction pattern and peak listing can be seen in FIG. 11, and Table 11A, respectively. Crystallographic information is listed in Table 11B.

TABLE 11A

Calculated PXRD Peak Listing of Compound 1 Hydrochloride Pattern K Peak Position (° 2θ)

| |
|---|
| 5.1 |
| 5.9 |
| 7.7 |
| 9.9 |
| 10.2 |
| 10.8 |
| 13.6 |
| 14.0 |
| 15.4 |
| 15.9 |
| 16.2 |
| 17.6 |
| 18.3 |
| 18.7 |
| 19.7 |
| 19.9 |
| 20.1 |
| 20.4 |
| 20.7 |
| 20.9 |
| 22.9 |
| 26.2 |

TABLE 11B

Structural information for Compound 1 Hydrochloride

| Crystal Form | Compound 1 Hydrochloride |
|---|---|
| Lattice Type | Triclinic |
| Space Group | P1 |
| a (Å) | 10.804 |
| b (Å) | 12.372 |
| c (Å) | 19.333 |
| α (°) | 76.540 |

TABLE 11B-continued

Structural information for Compound 1 Hydrochloride

| Crystal Form | Compound 1 Hydrochloride |
|---|---|
| β (°) | 87.159 |
| γ (°) | 70.074 |
| Volume (Å$^3$) | 2361.5 |
| Z | 2 |

Compound 1 Hydrochloride Hydrate

PXRD Pattern L

Example 15

Compound 1 hydrochloride solid (having pattern K) was exposed to the air under ambient conditions, and was confirmed to be Compound 1 hydrochloride hydrate.

Figure 12:
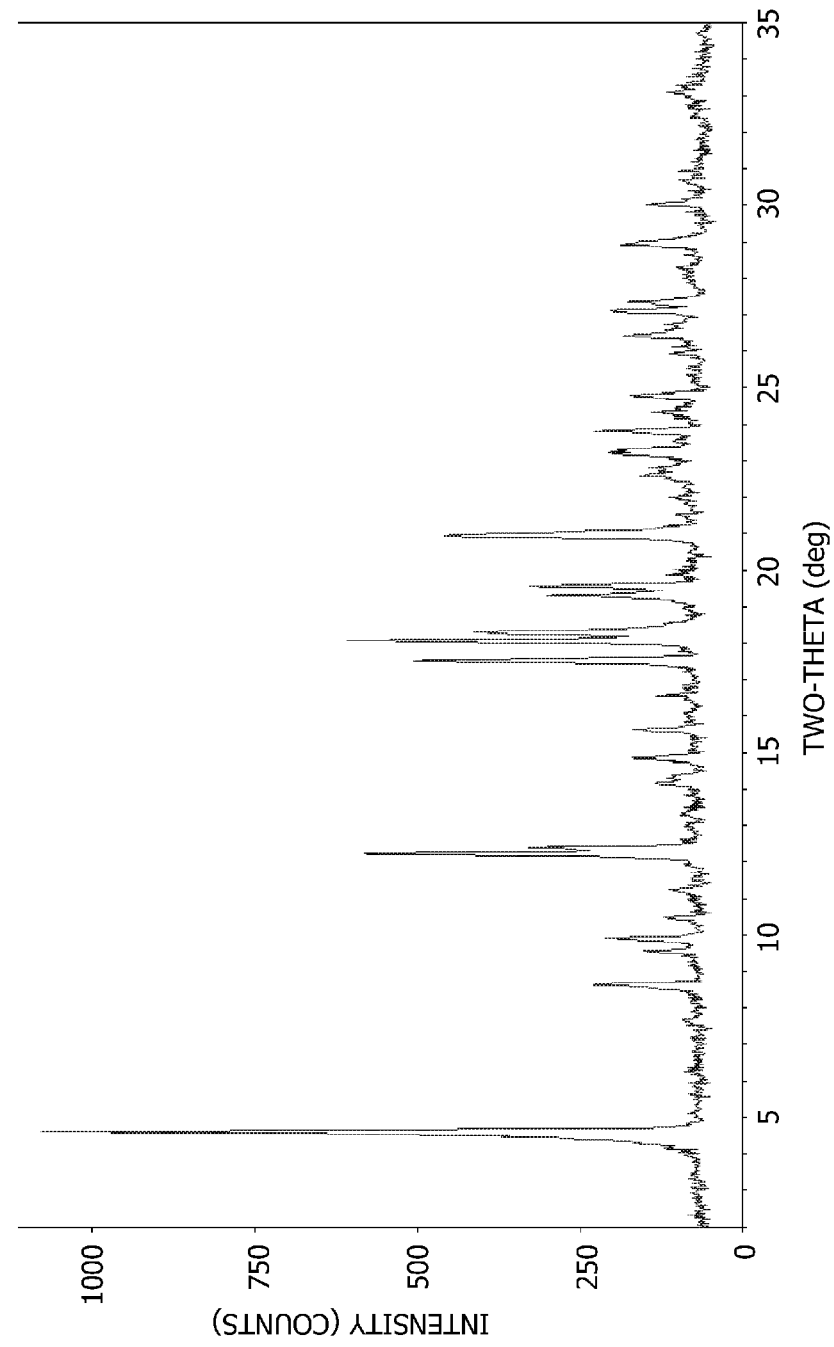
FIG. 12 is a PXRD scan of Compound 1 hydrochloride hydrate designated pattern L.

Powder X-ray diffraction pattern and peak listing can be seen in FIG. 12, and Table 12, respectively.

TABLE 12

PXRD Peak Listing for Compound 1 Hydrochloride Hydrate Pattern L Peak Position (° 2θ)

| |
|---|
| 4.6 |
| 8.7 |
| 9.6 |
| 9.9 |
| 12.3 |
| 14.9 |
| 15.7 |
| 17.6 |
| 18.1 |
| 18.4 |
| 19.3 |
| 19.6 |
| 21.0 |
| 23.3 |
| 23.9 |
| 24.8 |
| 26.5 |
| 27.2 |
| 27.4 |
| 29.0 |
| 30.1 |

Compound 1 Sulfate

PXRD Pattern M

Example 16

Compound 1 free base solid (16 mg, 0.018 mmol) was suspended in 0.5 mL of 2-propanol at 70° C. Sulfuric acid (1M, 25 µL) was added to the suspension while stirring (molar ratio of Compound 1:acid=1:1.4). Compound 1 quickly dissolved by reacting with sulfuric acid. Yellowish solids crystallized from the solution immediately after the dissolution occurred. The crystalline solid was confirmed to be Compound 1 sulfate with a stoichiometry of 1:1 using ion chromatography.

Figure 13:
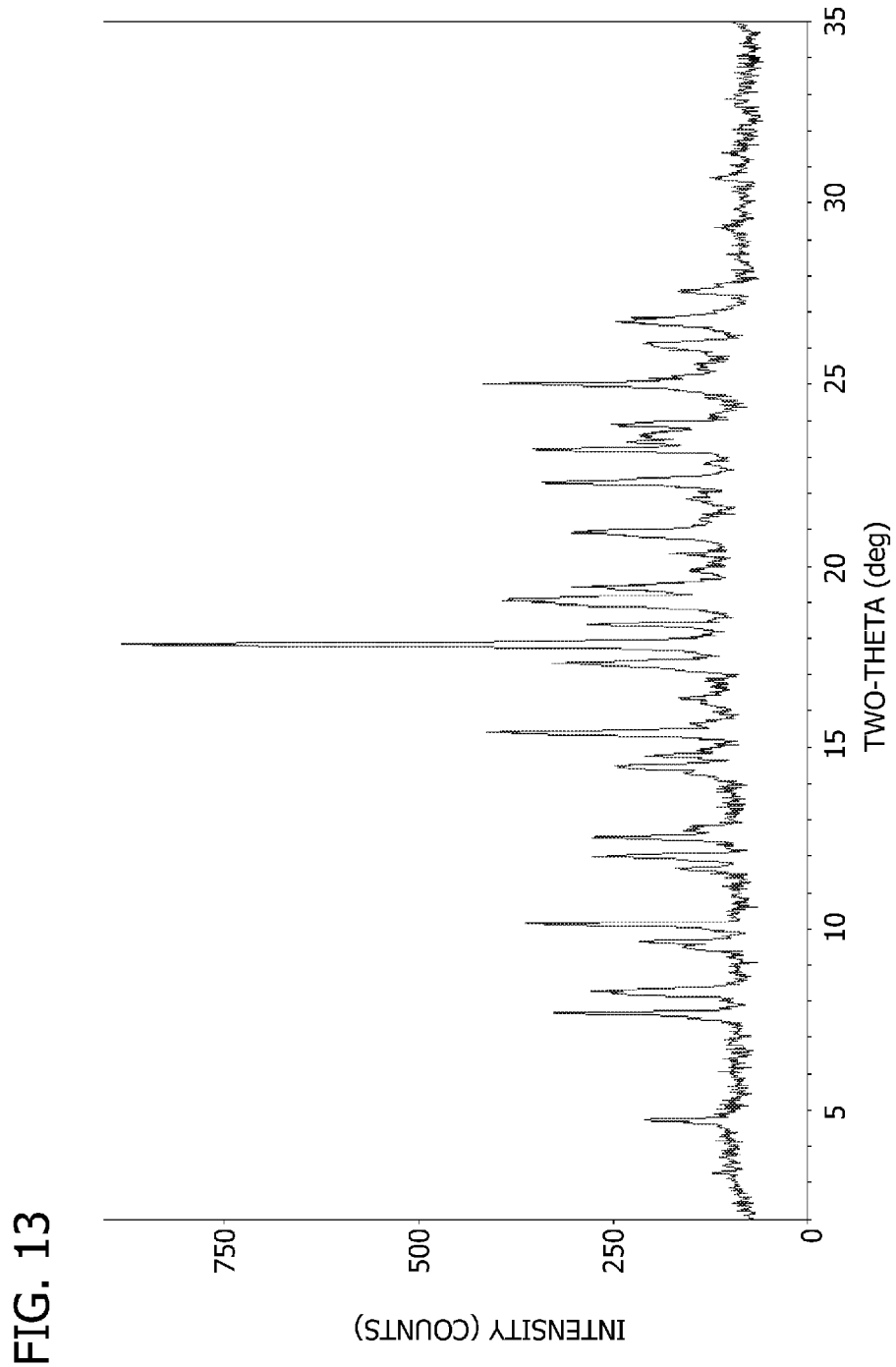
FIG. 13 is a PXRD scan of Compound 1 sulfate designated pattern M.

Powder X-ray diffraction pattern and peak listing can be seen in FIG. 13, and Table 13, respectively.

TABLE 13

PXRD Peak Listing for Compound 1 Sulfate Pattern M
Peak Position (° 2θ)

| |
|---|
| 4.8 |
| 7.7 |
| 8.3 |
| 9.7 |
| 10.2 |
| 12.0 |
| 12.6 |
| 14.5 |
| 15.4 |
| 17.4 |
| 17.9 |
| 18.4 |
| 19.1 |
| 19.5 |
| 21.0 |
| 22.4 |
| 23.3 |
| 23.9 |
| 25.1 |
| 26.8 |

Compound 1 Free Base THF Solvate

PXRD Pattern N

Example 17

Compound 1 free base solid was suspended in tetrahydrofuran (THF) at ambient temperatures to reach its solubility. After equilibrating, the solids were isolated at ambient temperature.

Figure 14:
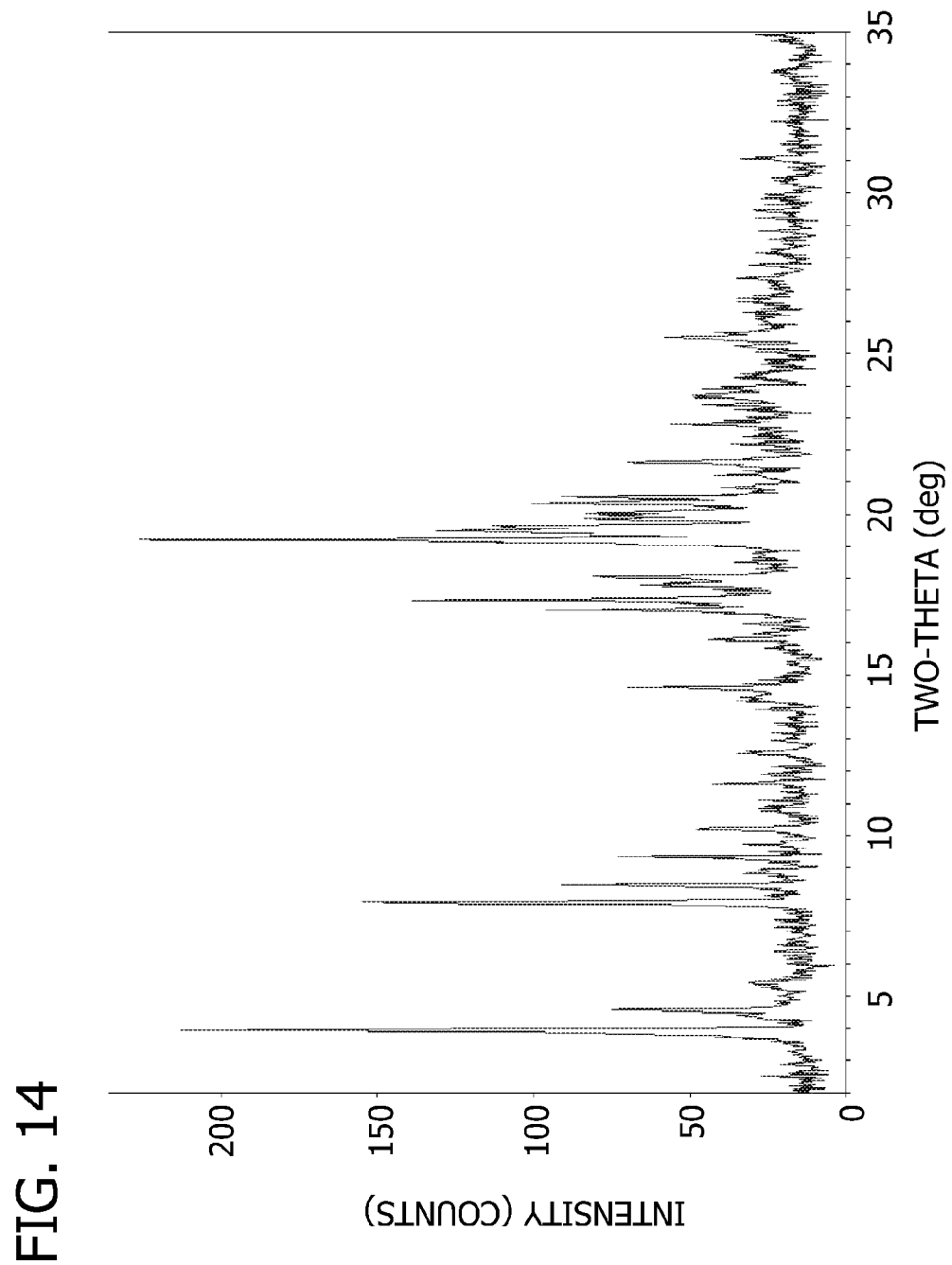
FIG. 14 is a PXRD scan of Compound 1 tetrahydrofuran solvate designated pattern N.

Powder X-ray diffraction pattern and peak listing are shown in FIG. 14 and Table 14, respectively.

TABLE 14

PXRD Peak Listing for Compound 1 Free Base THF Solvate Pattern N
Peak Position (° 2θ)

| |
|---|
| 4.0 |
| 4.6 |
| 8.0 |
| 8.5 |
| 9.4 |
| 14.6 |
| 17.1 |
| 17.4 |
| 17.8 |
| 18.1 |
| 19.2 |
| 19.5 |
| 20.1 |
| 20.4 |
| 20.5 |
| 21.7 |

PXRD data were collected using a G3000 diffractometer (Inel Corp., Artenay, France) equipped with a curved position-sensitive detector and parallel-beam optics. The diffractometer was operated with a copper anode tube (1.5 kW fine focus) at 40 kV and 30 mA. An incident-beam germanium monochromator provided monochromatic radiation Cu—K$_\alpha$ radiation, which has a wavelength of 1.54178 Å. The diffractometer was calibrated using the attenuated direct beam at one-degree intervals. Calibration was checked using a silicon powder line position reference standard (NIST 640c). The instrument was computer-controlled using Symphonix software (Inel Corp., Artenay, France) and the data were analyzed using Jade software (version 6.5, Materials Data, Inc., Livermore, Calif.). The sample was loaded onto an aluminum sample holder and leveled with a glass slide. PXRD peak position measurements are typically ±0.2 degrees two-theta (° 2θ).

In some embodiments, the percent crystallinity of any of the salt or crystalline forms of Compound 1 described herein can vary with respect to the total amount of Compound 1. In particular, certain embodiments provide for the percent crystallinity of a salt or crystalline form of Compound 1 being at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of Compound 1 appears to be crystalline as best can be determined using methods known in the art. Accordingly, pharmaceutical compositions and therapeutically effective amounts of Compound 1 can include amounts that vary in crystallinity. These include instances where Compound 1 is used as API in various formulations and solid forms, including where an amount of Compound 1 in a solid form is subsequently dissolved, partially dissolved, or suspended or dispersed in a liquid.

As noted, in some embodiments API compositions are provided that comprise Compound 1, wherein at least a portion of the Compound 1 in the API composition is in one of the salt or crystalline forms. For example, an API composition containing Compound 1 has at least 10%, at least 20%, at least 30%, at least 40%, at least 50%, at least 60%, at least 70%, at least 80%, at least 90%, at least 95% or at least 99% of the compound of the composition in one of the salt or crystalline forms. In some embodiments, essentially 100% of the Compound 1 of an API formulation is in a salt or crystalline form as described herein.

Any of the crystalline forms of Compound 1, including salts and solvated forms, can be useful as an active pharmaceutical ingredient (API) for preparation of pharmaceutical compositions. However, solvent-free forms are generally preferred for this purpose. A hydrate is considered solvent-free for this purpose. Solvated forms can be, as indicated above, useful as process intermediates in preparation of solvent-free forms. Compound 1 salts and crystalline forms can be used in preparation of pharmaceutical compositions suitable for various routes of administration, including oral, to a subject in need thereof. Thus, in some embodiments, a pharmaceutical composition is provided, comprising a crystalline form of Compound 1 and one or more pharmaceutically acceptable excipients. Such compositions can be prepared using various known processes of pharmacy.

In some embodiments, the salt or crystalline form of Compound 1 includes those of Compound 1 free base anhydrate having PXRD pattern A, Compound 1 free base anhydrate having PXRD pattern B, Compound 1 free base hydrate having PXRD pattern C, Compound 1 free base hydrate having PXRD pattern D, Compound 1 free base dichloromethane solvate having pattern E, Compound 1 free base ethyl acetate solvate having PXRD pattern F, Compound 1 free base ethyl acetate solvate having PXRD pattern G, Compound 1 free base acetonitrile solvate having PXRD pattern H, Compound 1 free base acetonitrile solvate having PXRD pattern I, Compound 1 free base acetone solvate having PXRD pattern J, Compound 1 hydrochloride having PXRD pattern K, Compound 1 hydrochloride hydrate having PXRD pattern L, Compound 1 sulfate having PXRD pattern M, and Compound 1 free base tetrahydrofuran (THF) solvate having PXRD pattern N, each having the respective powder X-ray diffraction patterns as described herein.

According to any of these embodiments, the composition can be deliverable, for example, by the oral route. Other routes of administration include without limitation parenteral, sublingual, buccal, intranasal, pulmonary, topical, transdermal, intradermal, ocular, otic, rectal, vaginal, intragastric, intracranial, intrasynovial and intra-articular routes.

Where it is desired to provide Compound 1 free base or salt in solution form, for example in a liquid formulation for oral or parenteral administration, the Compound 1 free base or salt will not, of course, be present in such a formulation in crystalline form; indeed, the presence of crystals is generally undesired in such a formulation. However, a crystalline form of Compound 1 free base can nonetheless be important as API in a process for preparing such a formulation. Thus, the present disclosure further provides a process for preparing a pharmaceutical solution composition of Compound 1 comprising dissolving a crystalline salt or a crystalline form of Compound 1 free base in a pharmaceutically acceptable solvent or mixture of solvents. Even where the desired formulation is one containing Compound 1 free base in amorphous form, for example a solid melt formulation, a crystalline form of Compound 1 free base can still be useful as API in a process for preparing such a formulation.

As API, a crystalline form of Compound 1 free base or mixtures thereof can have advantages over an amorphous form. For example, purification of API to the high degree of purity required by most regulatory authorities can be more efficient and therefore cost less where the API is in crystalline form as opposed to amorphous form. Physical and chemical stability, and therefore shelf-life of the API solid, can also be better for crystalline than amorphous forms. Ease of handling can be improved over the amorphous form, which can be oily or sticky. Drying can be more straightforward and more easily controlled in the case of the crystalline material, which can have a well-defined drying or desolvation temperature, than in the case of the amorphous material, which can have greater affinity for organic solvents and no well-defined drying temperature. Downstream processing using crystalline API can further permit enhanced process control. In preparing a liquid formulation, for example a solution in a lipid carrier, crystalline Compound 1 can dissolve faster and can have a reduced tendency to form a gel during dissolution. These advantages are illustrative and non-limiting.

Pharmaceutical compositions comprising crystalline Compound 1 free base, or prepared using crystalline Compound 1 free base or salts of Compound 1 as API, contain Compound 1 in an amount that can be therapeutically effective when the composition is administered to a subject in need thereof according to an appropriate regimen. Dosage amounts are expressed herein as free base equivalent amounts unless the context requires otherwise. Typically, a unit dose (the amount administered at a single time), which can be administered at an appropriate frequency, e.g., twice daily to once weekly, is about 10 to about 1,000 mg. Where frequency of administration is once daily (q.d.), unit dose and daily dose are the same. Illustratively, the unit dose of Compound 1 in a composition of the invention can be about 25 to about 1,000 mg, more typically about 50 to about 500 mg, for example about 50, about 100, about 150, about 200, about 250, about 300, about 350, about 400, about 450 or about 500 mg. Where the composition is prepared as a discrete dosage form such as a tablet or capsule, a unit dose can be deliverable in a single dosage form or a small plurality of dosage forms, most typically 1 to about 10 dosage forms.

The higher the unit dose, the more desirable it becomes to select excipients that permit a relatively high loading of API (in this case Compound 1 free base or salt) in the formulation. Typically, the concentration of Compound 1 in a formulation prepared according to the present disclosure is at least about 1%, e.g., about 1% to about 25%, by weight, but lower and higher concentrations can be acceptable or achievable in specific cases. Illustratively, the Compound 1 free base equivalent concentration in various embodiments is at least about 2%, e.g., about 2% to about 20%, by weight, for example about 5%, about 10% or about 15%, by weight of the formulation.

A composition prepared according to the invention comprises, in addition to the API, one or more pharmaceutically acceptable excipients. If the composition is to be prepared in solid form for oral administration, for example as a tablet or capsule, it typically includes at least one or more solid diluents and one or more solid disintegrants. Optionally, the excipients further include one or more binding agents, wetting agents and/or antifrictional agents (lubricants, anti-adherents and/or glidants). Many excipients have two or more functions in a pharmaceutical composition. Characterization herein of a particular excipient as having a certain function, e.g., diluent, disintegrant, binding agent, etc., should not be read as limiting to that function. Further information on excipients can be found in standard reference works such as *Handbook of Pharmaceutical Excipients*, 3rd ed. (Kibbe, ed. (2000), Washington: American Pharmaceutical Association).

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of $\alpha$- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 5% to about 95%, for example about 20% to about 90%, or about 50% to about 85%, by weight of the composition. The diluent or diluents selected preferably exhibit suitable flow properties and, where tablets are desired, compressibility.

Microcrystalline cellulose and silicified microcrystalline cellulose are particularly useful diluents, and are optionally used in combination with a water-soluble diluent such as mannitol. Illustratively, a suitable weight ratio of microcrystalline cellulose or silicified microcrystalline cellulose to mannitol is about 10:1 to about 1:1, but ratios outside this range can be useful in particular circumstances.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

Sodium starch glycolate is a particularly useful disintegrant, and typically constitutes in total about 1% to about 20%, for example about 2% to about 15%, or about 5% to about 10%, by weight of the composition.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

Povidone and hydroxypropylcellulose, either individually or in combination, are particularly useful binding agents for tablet formulations, and, if present, typically constitute about 0.5% to about 15%, for example about 1% to about 10%, or about 2% to about 8%, by weight of the composition.

Wetting agents, if present, are normally selected to maintain the drug in close association with water, a condition that can improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; tyloxapol; and the like. One or more wetting agents, if present, typically constitute in total about 0.1% to about 15%, for example about 0.2% to about 10%, or about 0.5% to about 7%, by weight of the composition.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition. Colloidal silicon dioxide is a particularly useful glidant.

Other excipients such as buffering agents, stabilizers, antioxidants, antimicrobials, colorants, flavors and sweeteners are known in the pharmaceutical art and can be used in compositions of the present invention. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

A solid orally deliverable composition of the present invention is not limited by any process used to prepare it. Any suitable process of pharmacy can be used, including dry blending with or without direct compression, and wet or dry granulation.

If the composition is to be prepared in liquid (including encapsulated liquid) form, the API (e.g., crystalline Compound 1 free base or salt) can be, for example, dissolved in a suitable carrier, typically one comprising a lipid solvent for the API. The higher the unit dose, the more desirable it becomes to select a carrier that permits a relatively high concentration of the drug in solution therein. Typically, the free base equivalent concentration of API in the carrier is at least about 10 mg/ml, e.g., about 10 to about 500 mg/ml, but lower and higher concentrations can be acceptable or achievable in specific cases. Illustratively, the drug concentration in various embodiments is at least about 10 mg/ml, e.g., about 10 to about 250 mg/ml, or at least about 20 mg/ml, e.g., about 20 to about 200 mg/ml, for example about 20, about 25, about 30, about 40, about 50, about 75, about 100 or about 150 mg/ml.

The carrier can be substantially non-aqueous, i.e., having no water, or having an amount of water that is small enough to be, in practical terms, essentially non-deleterious to performance or properties of the composition. Typically, the carrier comprises zero to less than about 5% by weight water. It will be understood that certain ingredients useful herein can bind small amounts of water on or within their molecules or supramolecular structures; such bound water if present does not affect the "substantially non-aqueous" character of a carrier as defined herein.

In some embodiments, the carrier comprises one or more glyceride materials. Suitable glyceride materials include, without limitation, medium to long chain mono-, di- and triglycerides. The term "medium chain" herein refers to hydrocarbyl chains individually having no less than about 6 and less than about 12 carbon atoms, including for example $C_8$ to $C_{10}$ chains. Thus glyceride materials comprising caprylyl and capryl chains, e.g., caprylic/capric mono-, di- and/or triglycerides, are examples of "medium chain" glyceride materials. The term "long chain" herein refers to hydrocarbyl chains individually having at least about 12, for example about 12 to about 18, carbon atoms, including for example lauryl, myristyl, cetyl, stearyl, oleyl, linoleyl and linolenyl chains. Medium to long chain hydrocarbyl groups in the glyceride materials can be saturated, mono- or polyunsaturated.

In one embodiment the carrier comprises a medium chain and/or a long chain triglyceride material. A suitable example of a medium chain triglyceride material is a caprylic/capric triglyceride product such as, for example, Captex 355 EP™ of Abitec Corp. and products substantially equivalent thereto. Suitable examples of long chain triglycerides include any pharmaceutically acceptable vegetable oil, for example canola, coconut, corn, cottonseed, flaxseed, olive, palm, peanut, safflower, sesame, soy and sunflower oils, and mixtures of such oils. Oils of animal, particularly marine animal, origin can also be used, including for example fish oil.

In some embodiments the carrier comprises a phospholipid and a pharmaceutically acceptable solubilizing agent for the phospholipid. It will be understood that reference in the singular to a (or the) phospholipid, solubilizing agent or other formulation ingredient herein includes the plural; thus combinations, for example mixtures, of more than one phospholipid, or more than one solubilizing agent, are expressly contemplated herein. The solubilizing agent, or the combination of solubilizing agent and phospholipid, also solubilizes the drug, although other carrier ingredients, such as a surfactant or an alcohol such as ethanol, optionally present in the carrier can in some circumstances provide enhanced solubilization of the drug.

Any pharmaceutically acceptable phospholipid or mixture of phospholipids can be used. In general such phospholipids are phosphoric acid esters that yield on hydrolysis phosphoric acid, fatty acid(s), an alcohol and a nitrogenous base. Pharmaceutically acceptable phospholipids can include without limitation phosphatidylcholines, phosphatidylserines and phosphatidylethanolamines. In one embodiment the composition comprises phosphatidylcholine, derived for example from natural lecithin. Any source of lecithin can be used, including animal sources such as egg yolk, but plant sources are generally preferred. Soy is a particularly rich source of lecithin that can provide phosphatidylcholine for use in the present invention.

Illustratively, a suitable amount of phospholipid is about 15% to about 75%, for example about 30% to about 60%, by weight of the carrier, although greater and lesser amounts can be useful in particular situations.

Ingredients useful as components of the solubilizing agent are not particularly limited and will depend to some extent on the desired concentration of drug and of phospholipid. In one embodiment, the solubilizing agent comprises one or more glycols and/or one or more glyceride materials.

Suitable glycols include propylene glycol and polyethylene glycols (PEGs) having molecular weight of about 200 to about 1,000 g/mol, e.g., PEG-400, which has an average molecular weight of about 400 g/mol. Such glycols can provide relatively high solubility of the drug; however the potential for oxidative degradation of the drug can be increased when in solution in a carrier comprising such glycols, for example because of the tendency of glycols to produce superoxides, peroxides and/or free hydroxyl radicals. The higher the glycol content of the carrier, the greater may be the tendency for degradation of a chemically unstable drug. In one embodiment, therefore, one or more glycols are present in a total glycol amount of at least about 1% but less than about 50%, for example less than about 30%, less than about 20%, less than about 15% or less than about 10% by weight of the carrier. In another embodiment, the carrier comprises substantially no glycol.

Suitable glyceride materials for use together with a phospholipid include, without limitation, those mentioned above. Where one or more glyceride materials are present as a major component of the solubilizing agent, a suitable total amount of glycerides is an amount effective to solubilize the phospholipid and, in combination with other components of the carrier, effective to maintain the drug and antioxidant in solution. For example, glyceride materials such as medium chain and/or long chain triglycerides can be present in a total glyceride amount of about 5% to about 70%, for example about 15% to about 60% or about 25% to about 50%, by weight of the carrier.

Additional solubilizing agents that are other than glycols or glyceride materials can be included if desired. Such agents, for example N-substituted amide solvents such as dimethylformamide (DMF) and N,N-dimethylacetamide (DMA), can, in specific cases, assist in raising the limit of solubility of the drug in the carrier, thereby permitting increased drug loading. However, N-substituted amides including DMF and DMA can present regulatory and/or toxicological issues that restrict the amount of such solvents that can be used in a formulation. Furthermore, the carriers useful herein generally provide adequate solubility of small-molecule drugs of interest herein without such additional agents.

Even when a sufficient amount of a glycol or glyceride material is present to solubilize the phospholipid, the resulting carrier solution and/or the drug-carrier system may be rather viscous and difficult or inconvenient to handle. In such cases it may be found desirable to include in the carrier a viscosity reducing agent in an amount effective to provide acceptably low viscosity. An example of such an agent is an alcohol, more particularly ethanol, which is preferably introduced in a form that is substantially free of water, for example 99% ethanol, dehydrated alcohol USP or absolute ethanol. Excessively high concentrations of ethanol should, however, generally be avoided. This is particularly true where, for example, the drug-carrier system is to be administered in a gelatin capsule, because of the tendency of high ethanol concentrations to result in mechanical failure of the capsule. In general, suitable amounts of ethanol are 0% to about 25%, for example about 1% to about 20% or about 3% to about 15%, by weight of the carrier.

Optionally, the carrier further comprises a pharmaceutically acceptable non-phospholipid surfactant. One of skill in the art will be able to select a suitable surfactant for use in a composition of the invention. Illustratively, a surfactant such as polysorbate 80 can be included in an amount of 0% to about 5%, for example 0% to about 2% or 0% to about 1%, by weight of the carrier.

Conveniently, pre-blended products are available containing a suitable phospholipid+solubilizing agent combination for use in compositions of the present invention. Pre-blended phospholipid+solubilizing agent products can be advantageous in improving ease of preparation of the present compositions.

An illustrative example of a pre-blended phospholipid+solubilizing agent product is Phosal 50 PG™, available from Phospholipid GmbH, Germany, which comprises, by weight, not less than 50% phosphatidylcholine, not more than 6% lysophosphatidylcholine, about 35% propylene glycol, about 3% mono- and diglycerides from sunflower oil, about 2% soy fatty acids, about 2% ethanol, and about 0.2% ascorbyl palmitate.

Another illustrative example is Phosal 53 MCT™, also available from Phospholipid GmbH, which contains, by weight, not less than 53% phosphatidylcholine, not more than 6% lysophosphatidylcholine, about 29% medium chain triglycerides, 3-6% (typically about 5%) ethanol, about 3% mono- and diglycerides from sunflower oil, about 2% oleic acid, and about 0.2% ascorbyl palmitate (reference composition). A product having the above or substantially equivalent composition, whether sold under the Phosal 53 MCT™ brand or otherwise, is generically referred to herein as "phosphatidylcholine+medium chain triglycerides 53/29". A product having "substantially equivalent composition" in the present context means having a composition sufficiently similar to the reference composition in its ingredient list and relative amounts of ingredients to exhibit no practical difference in properties with respect to utilization of the product herein.

Yet another illustrative example is Phosal 50 SA+™, also available from Phospholipid GmbH, which contains, by weight, not less than 50% phosphatidylcholine and not more than 6% lysophosphatidylcholine in a solubilizing system comprising safflower oil and other ingredients.

The phosphatidylcholine component of each of these pre-blended products can be derived from soy lecithin. Products of substantially equivalent composition may be obtainable from other suppliers.

A pre-blended product such as Phosal 50 PG™, Phosal 53 MCT™ or Phosal 50 SA+™ can, in some embodiments, constitute substantially the entire carrier system. In other embodiments, additional ingredients are present, for example ethanol (additional to any that may be present in the pre-blended product), non-phospholipid surfactant such as polysorbate 80, polyethylene glycol and/or other ingredients. Such additional ingredients, if present, are typically included in only minor amounts. Illustratively, phosphatidylcholine+medium chain triglycerides 53/29 can be included in the carrier in an amount of about 50% to 100%, for example about 80% to 100%, by weight of the carrier.

Without being bound by theory, it is believed that the therapeutic efficacy of Compound 1 is due at least in part to its ability to bind to a Bcl-2 family protein such as Bcl-2, Bcl-$X_L$ or Bcl-w in a way that inhibits the anti-apoptotic action of the protein, for example by occupying the BH3 binding groove of the protein.

In still further embodiments of the invention, there is provided a method for treating a disease characterized by apoptotic dysfunction and/or overexpression of an anti-apoptotic Bcl-2 family protein, comprising administering to a subject having the disease a therapeutically effective amount of crystalline Compound 1 free base or a pharmaceutical composition comprising a salt or crystalline form of Compound 1 free base and one or more pharmaceutically acceptable excipients.

In still further embodiments of the invention, there is provided a method for treating a disease characterized by apoptotic dysfunction and/or overexpression of an anti-apoptotic Bcl-2 family protein is provided, where the method comprises preparing a solution or dispersion of a salt or crystalline form of Compound 1 described herein in a pharmaceutically acceptable solvent or mixture of solvents, and administering the resulting solution or dispersion in a therapeutically effective amount to a subject having the disease.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or overexpression of an anti-apoptotic Bcl-2 family protein. A human subject can be male or female and of any age, but is typically an adult.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the bioavailability of the particular formulation, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus, the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of Compound 1 are generally about 25 to about 1000 mg/day or about 50 to about 1000 mg/day, more typically about 50 to about 500 mg/day or about 200 to about 400 mg/day, for example about 50, about 100, about 150, about 200, about 250, about 300, about 350, about 400, about 450, about 500, about 750 or about 1000 mg/day, administered at an average dosage interval of about 3 hours to about 7 days, for example about 8 hours to about 3 days, or about 12 hours to about 2 days. In most cases a once-daily (q.d.) administration regimen is suitable.

In certain embodiments, the invention relates to a method for treating a disease characterized by apoptotic dysfunction and/or overexpression of an anti-apoptotic Bcl-2 family protein, comprising administering to a subject having the disease a therapeutically effective amount of (a) Compound 1 in a salt or crystalline form or (b) a pharmaceutical composition comprising Compound 1 in a salt or crystalline form and one or more pharmaceutically acceptable excipients, wherein the therapeutically effective amount is administered orally in a dose of about 50 to about 1000 mg Compound 1 per day at an average treatment interval of about 3 hours to about 7 days.

In certain embodiments, the invention relates to a method for treating a disease characterized by apoptotic dysfunction and/or overexpression of an anti-apoptotic Bcl-2 family protein, comprising administering to a subject having the disease a therapeutically effective amount of (a) Compound 1 in a salt or crystalline form or (b) a pharmaceutical composition comprising Compound 1 in a salt or crystalline form and one or more pharmaceutically acceptable excipients, wherein the therapeutically effective amount is administered orally once daily in a dose of about 200 to about 400 mg Compound 1 free base equivalent per day.

In certain embodiments, the invention relates to a method for treating a disease characterized by apoptotic dysfunction and/or overexpression of an anti-apoptotic Bcl-2 family protein, comprising administering a solution or dispersion of Compound 1 in a salt or crystalline form to a subject having the disease, wherein the solution is administered orally in a dose of about 50 to about 1000 mg Compound 1 per day at an average treatment interval of about 3 hours to about 7 days.

In certain embodiments, the invention relates to a method for treating a disease characterized by apoptotic dysfunction and/or overexpression of an anti-apoptotic Bcl-2 family protein, comprising administering a solution or dispersion of Compound 1 in a salt or crystalline form to a subject having the disease, wherein the solution is administered orally once daily in a dose of about 200 to about 400 mg Compound 1 free base equivalent per day.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

Compositions prepared according to the present invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

Combination therapies illustratively include administration of a composition comprising (or prepared using as API) one or more crystalline forms of Compound 1 (including crystalline salt forms) concomitantly with one or more of bortezomid, carboplatin, cisplatin, cyclophosphamide, dacarbazine, dexamethasone, docetaxel, doxorubicin, etoposide, fludarabine, hydroxydoxorubicin, irinotecan, paclitaxel, rapamycin, rituximab, vincristine and the like, for example with a polytherapy such as CHOP (cyclophosphamide+hydroxydoxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

A Compound 1 composition can be administered in combination therapy with one or more therapeutic agents that include, but are not limited to, angiogenesis inhibitors, antiproliferative agents, other apoptosis promoters (for example, Bcl-xL, Bcl-w and Bfl-1 inhibitors), activators of a death receptor pathway, BiTE (bi-specific T-cell engager) antibodies, dual variable domain binding proteins (DVDs), inhibitors of apoptosis proteins (IAPs), microRNAs, mitogen-activated extracellular signal-regulated kinase inhibitors, multivalent binding proteins, poly-ADP (adenosine diphosphate)-ribose polymerase (PARP) inhibitors, small inhibitory ribonucleic acids (siRNAs), kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDs), antimitotic agents, alkylating agents, antimetabolites, intercalating antibiotics, platinum-containing chemotherapeutic agents, growth factor inhibitors, ionizing radiation, cell cycle inhibitors, enzymes, topoisomerase inhibitors, biologic response modifiers, immunologicals, antibodies, hormonal therapies, retinoids, deltoids, plant alkaloids, proteasome inhibitors, HSP-90 inhibitors, histone deacetylase (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, gefitinib, erlotinib, cetuximab, EMD-7200, ABX-EGF, HR3, IgA antibodies, TP-38 (IVAX), EGFR fusion protein, EGF-vaccine, anti-EGFR immunoliposomes and lapatinib.

Examples of PDGFR inhibitors include, but are not limited to, CP-673451 and CP-868596.

Examples of VEGFR inhibitors include, but are not limited to, bevacizumab, sunitinib, sorafenib, CP-547632, axitinib, vandetanib, AEE788, AZD-2171, VEGF trap, vatalanib, pegaptanib, IM862, pazopanib, ABT-869 and angiozyme.

Bcl-2 family protein inhibitors other than Compound 1 include, but are not limited to, ABT-263, AT-101 ((−)gossypol), Genasense™ Bcl-2-targeting antisense oligonucleotide (G3139 or oblimersen), IPI-194, IPI-565, N-(4-(4-((4'-chloro (1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), GX-070 (obatoclax) and the like.

Activators of a death receptor pathway include, but are not limited to, TRAIL, antibodies or other agents that target death receptors (e.g., DR4 and DR5) such as apomab, conatumumab, ETR2-ST01, GDC0145 (lexatumumab), HGS-1029, LBY-135, PRO-1762 and trastuzumab.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to, BI-2536.

Examples of bcr-abl kinase inhibitors include, but are not limited to, imatinib and dasatinib.

Examples of platinum-containing agents include, but are not limited to, cisplatin, carboplatin, eptaplatin, lobaplatin, nedaplatin, oxaliplatin and satraplatin.

Examples of mTOR inhibitors include, but are not limited to, CCI-779, rapamycin, temsirolimus, everolimus, RAD001 and AP-23573.

Examples of HSP-90 inhibitors include, but are not limited to, geldanamycin, radicicol, 17-AAG, KOS-953, 17-DMAG, CNF-101, CNF-1010, 17-AAG-nab, NCS-683664, efungumab, CNF-2024, PU3, PU24FC1, VER-49009, IPI-504, SNX-2112 and STA-9090.

Examples of HDAC inhibitors include, but are not limited to, suberoylanilide hydroxamic acid (SAHA), MS-275, valproic acid, TSA, LAQ-824, trapoxin and depsipeptide.

Examples of MEK inhibitors include, but are not limited to, PD-325901, ARRY-142886, ARRY-438162 and PD-98059.

Examples of CDK inhibitors include, but are not limited to, flavopyridol, MCS-5A, CVT-2584, seliciclib ZK-304709, PHA-690509, BMI-1040, GPC-286199, BMS-387032, PD-332991 and AZD-5438.

Examples of COX-2 inhibitors include, but are not limited to, celecoxib, parecoxib, deracoxib, ABT-963, etoricoxib, lumiracoxib, BMS-347070, RS 57067, NS-398, valdecoxib, rofecoxib, SD-8381, 4-methyl-2-(3,4-dimethylphenyl)-1-(4-sulfamoyl-phenyl-1H-pyrrole, T-614, JTE-522, S-2474, SVT-2016, CT-3 and SC-58125.

Examples of NSAIDs include, but are not limited to, salsalate, diflunisal, ibuprofen, ketoprofen, nabumetone, piroxicam, naproxen, diclofenac, indomethacin, sulindac, tolmetin, etodolac, ketorolac and oxaprozin.

Examples of ErbB2 receptor inhibitors include, but are not limited to, CP-724714, canertinib, trastuzumab, petuzumab, TAK-165, ionafamib, GW-282974, EKB-569, PI-166, dHER2, APC-8024, anti-HER/2neu bispecific antibody B7.her2IgG3 and HER2 trifunctional bispecific antibodies mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine™ (laromustine), AMD-473, altretamine, AP-5280, apaziquone, brostallicin, bendamustine, carmustine, estramustine, fotemustine, glufosfamide, KW-2170, mafosfamide, mitolactol, lomustine, treosulfan, dacarbazine and temozolomide.

Examples of antimetabolites include, but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, pemetrexed, gemcitabine, fludarabine, 5-azacitidine, capecitabine, cladribine, clofarabine, decitabine, eflornithine, ethenylcytidine, cytosine arabinoside, hydroxyurea, TS-1, melphalan, nelarabine, nolatrexed, disodium pemetrexed, pentostatin, pelitrexol, raltitrexed, triapine, trimetrexate, vidarabine, mycophenolic acid, ocfosfate, pentostatin, tiazofurin, ribavirin, EICAR, hydroxyurea and deferoxamine.

Examples of antibiotics include, but are not limited to, intercalating antibiotics, aclarubicin, actinomycin D, amrubicin, annamycin, adriamycin, bleomycin, daunorubicin, doxorubicin (including liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, aclarubicin, amonafide, belotecan, camptothecin, 10-hydroxycamptothecin, 9-amino-camptothecin, amsacrine, dexrazoxane, diflomotecan, irinotecan HCl, edotecarin, epirubicin, etoposide, exatecan, becatecarin, gimatecan, lurtotecan, orathecin, BN-80915, mitoxantrone, pirarbucin, pixantrone, rubitecan, sobuzoxane, SN-38, tafluposide and topotecan.

Examples of antibodies include, but are not limited to, rituximab, cetuximab, bevacizumab, trastuzumab, CD40-specific antibodies and IGF1R-specific antibodies, chTNT-1/B, denosumab, edrecolomab, WX G250, zanolimumab, lintuzumab and ticilimumab.

Examples of hormonal therapies include, but are not limited to, sevelamer carbonate, rilostane, luteinizing hormone releasing hormone, modrastane, exemestane, leuprolide acetate, buserelin, cetrorelix, deslorelin, histrelin, anastrozole, fosrelin, goserelin, degarelix, doxercalciferol, fadrozole, formestane, tamoxifen, arzoxifene, bicalutamide, abarelix, triptorelin, finasteride, fulvestrant, toremifene, raloxifene, trilostane, lasofoxifene, letrozole, flutamide, megesterol, mifepristone, nilutamide, dexamethasone, prednisone and other glucocorticoids.

Examples of retinoids or deltoids include, but are not limited to, seocalcitol, lexacalcitol, fenretinide, aliretinoin, tretinoin, bexarotene and LGD-1550.

Examples of plant alkaloids include, but are not limited to, vincristine, vinblastine, vindesine and vinorelbine.

Examples of proteasome inhibitors include, but are not limited to, bortezomib, MG-132, NPI-0052 and PR-171.

Examples of immunologicals include, but are not limited to, interferons and numerous other immune-enhancing agents. Interferons include interferon alpha, interferon alpha-2a, interferon alpha-2b, interferon beta, interferon gamma-1a, interferon gamma-1b, interferon gamma-n1 and combinations thereof. Other agents include filgrastim, lentinan, sizofilan, BCG live, ubenimex, WF-10 (tetrachlorodecaoxide or TCDO), aldesleukin, alemtuzumab, BAM-002, dacarbazine, daclizumab, denileukin, gemtuzumab ozogamicin, ibritumomab, imiquimod, lenograstim, melanoma vaccine, molgramostim, sargaramostim, tasonermin, tecleukin, thymalasin, tositumomab, Virulizin™ immunotherapeutic of Lorus Pharmaceuticals, Z-100 (specific substance of Maruyama or SSM), Zevalin™ (90Y-ibritumomab tiuxetan), epratuzumab, mitumomab, oregovomab, pemtumomab, Provenge™ (sipuleucel-T), teceleukin, Therocys™ (Bacillus Calmette-Guerin), cytotoxic lymphocyte antigen 4 (CTLA4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include, but are not limited to, krestin, lentinan, sizofuran, picibanil, PF-3512676 and ubenimex.

Examples of pyrimidine analogs include, but are not limited to, 5-fluorouracil, floxuridine, doxifluridine, raltitrexed, cytarabine, cytosine arabinoside, fludarabine, triacetyluridine, troxacitabine and gemcitabine.

Examples of purine analogs include, but are not limited to, mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, larotaxel, epothilone D, PNU-100940, batabulin, ixabepilone, patupilone, XRP-9881, vinflunine and ZK-EPO (synthetic epothilone).

Examples of radiotherapy include, but are not limited to, external beam radiotherapy (XBRT), teletherapy, brachytherapy, sealed-source radiotherapy and unsealed-source radiotherapy.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of the apoptosis-promoting agent ABT-263 (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

PARP inhibitors include, but are not limited to, ABT-888, olaparib, KU-59436, AZD-2281, AG-014699, BSI-201, BGP-15, INO-1001, ONO-2231 and the like.

Additionally or alternatively, a composition of the present invention can be administered in combination therapy with one or more antitumor agents selected from ABT-100, N-acetylcolchinol-O-phosphate, acitretin, AE-941, aglycon protopanaxadiol, arglabin, arsenic trioxide, AS04 adjuvant-adsorbed HPV vaccine, L-asparaginase, atamestane, atrasentan, AVE-8062, bosentan, canfosfamide, Canvaxin™, catumaxomab, CeaVac™ celmoleukin, combrestatin A4P, contusugene ladenovec, Cotara™, cyproterone, deoxycoformycin, dexrazoxane, N,N-diethyl-2-(4-(phenylmethyl)phenoxy)ethanamine, 5,6-dimethylxanthenone-4-acetic acid, docosahexaenoic acid/paclitaxel, discodermolide, efaproxiral, enzastaurin, epothilone B, ethynyluracil, exisulind, falimarev, Gastrimmune™ GMK vaccine, GVAX™, halofuginone, histamine, hydroxycarbamide, ibandronic acid, ibritumomab tiuxetan, IL-13-PE38, inalimarev, interleukin 4, KSB-311, lanreotide, lenalidomide, lonafarnib, lovastatin, 5,10-methylenetetrahydrofolate, mifamurtide, miltefosine, motexafin, oblimersen, OncoVAX™, Osidem™, paclitaxel albumin-stabilized nanoparticle, paclitaxel poliglumex, pamidronate, panitumumab, peginterferon alfa, pegaspargase, phenoxodiol, poly(I)-poly(C12U), procarbazine, ranpirnase, rebimastat, recombinant quadrivalent HPV vaccine, squalamine, staurosporine, STn-KLH vaccine, T4 endonuclase V, tazarotene, 6,6',7,12-tetramethoxy-2,2'-dimethyl-1β-berbaman, thalidomide, TNFerade™, $^{131}$I-tositumomab, trabectedin, triazone, tumor necrosis factor, Ukrain™, vaccinia-MUC-1 vaccine, L-valine-L-boroproline, Vitaxin™, vitespen, zoledronic acid and zorubicin.

In one embodiment, a composition comprising (or prepared using as API) one or more crystalline forms of Compound 1 (including crystalline salts) is administered in a therapeutically effective amount to a subject in need thereof to treat a disease during which is overexpressed one or more of antiapoptotic Bcl-2 protein, antiapoptotic Bcl-X$_L$ protein and antiapoptotic Bcl-w protein.

In another embodiment, a composition comprising (or prepared using as API) one or more crystalline forms of Compound 1 (including crystalline salts) is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, a composition comprising (or prepared using as API) one or more crystalline forms of Compound 1 (including crystalline salts) is administered in a therapeutically effective amount to a subject in need thereof to treat bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

According to any of these embodiments, the composition is administered in combination therapy with one or more additional therapeutic agents.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of (a) a composition comprising (or prepared using as API) crystalline Compound 1 free base and (b) one or more of etoposide, vincristine, CHOP, rituximab, rapamycin, R-CHOP, RCVP, DA-EPOCH-R or bortezomib.

In particular embodiments, a composition comprising (or prepared using as API) crystalline Compound 1 free base is administered in a therapeutically effective amount to a subject in need thereof in combination therapy with etoposide, vincristine, CHOP, rituximab, rapamycin, R-CHOP, RCVP, DA-EPOCH-R or bortezomib in a therapeutically effective amount, for treatment of a lymphoid malignancy such as B-cell lymphoma or non-Hodgkin's lymphoma.

In another embodiment, a composition of the invention is administered in a therapeutically effective amount to a subject in need thereof to treat an immune or autoimmune disorder. Such disorders include acquired immunodeficiency disease syndrome (AIDS), autoimmune lymphoproliferative syndrome, hemolytic anemia, inflammatory diseases, thrombocytopenia, acute and chronic immune diseases associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis-associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycemia, autoimmune neutropenia, autoimmune thrombocytopenia, autoimmune thyroid disease, B-cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy-associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinemia), conjunctivitis, connective tissue disease-associated interstitial lung disease, contact dermatitis, Coombs-positive hemolytic anemia, cor pulmonale, Creutzfeldt-Jakob disease, cryptogenic autoimmune hepatitis, cryptogenic fibrosing alveolitis, culture-negative sepsis, cystic fibrosis, cytokine therapy-associated disorders, Crohn's disease, dementia pugilistica, demyelinating diseases, dengue hemorrhagic fever, dermatitis, dermatitis scleroderma, dermatologic conditions, dermatomyositis/polymyositis-associated lung disease, diabetes, diabetic arteriosclerotic disease, diabetes mellitus, diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram-negative sepsis, gram-positive sepsis, granulomas due to intracellular organisms, group B streptococci (GBS) infection, Graves' disease, hemosiderosis-associated lung disease, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpura, hepatitis A, hepatitis B, hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopenia, idiopathic pulmonary fibrosis, idiopathic thrombocytopenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease-associated lung disease, monoclonal gammopathy, multiple myeloma, multiple systems degenerations (Mencel, Dejerine-Thomas, Shy-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, non-alcoholic steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post-perfusion syndrome, post-pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, progressive supranuclear palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis-associated interstitial lung disease, rheumatoid spondylitis, sarcoidosis, Schmidt's syndrome, scleroderma, senile chorea, senile dementia of Lewy body type, sepsis syndrome, septic shock, seronegative arthropathies, shock, sickle cell anemia, Sjögren's disease-associated lung disease, Sjögren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic polyglandular deficiency type I, sporadic polyglandular deficiency type II, Still's disease, streptococcal myositis, stroke, structural lesions of the cerebellum, subacute sclerosing panencephalitis, sympathetic ophthalmia, syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, telangiectasia, Th2-type and Th1-type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

The present invention also provides a method for maintaining in bloodstream of a human cancer patient a therapeutically effective plasma concentration of Compound 1 and/or one or more metabolites thereof, comprising administering to the subject a pharmaceutical composition as described herein, in a dosage amount equivalent to about 50 to about 500 mg Compound 1 per day, at an average dosage interval of about 3 hours to about 7 days.

What constitutes a therapeutically effective plasma concentration depends inter alia on the particular cancer present in the patient, the stage, severity and aggressiveness of the cancer, and the outcome sought (e.g., stabilization, reduction in tumor growth, tumor shrinkage, reduced risk of metastasis, etc.). It is strongly preferred that, while the plasma concentration is sufficient to provide benefit in terms of treating the cancer, it should not be sufficient to provoke an adverse side-effect to an unacceptable or intolerable degree.

For treatment of cancer in general and of a lymphoid malignancy such as non-Hodgkin's lymphoma in particular, the plasma concentration of Compound 1 should in most cases be maintained in a range of about 0.5 to about 10 µg/ml. Thus, during a course of Compound 1 therapy, the steady-state $C_{max}$ should in general not exceed about 10 µg/ml, and the steady-state $C_{min}$ should in general not fall below about 0.5 µg/ml. It will further be found desirable to select, within the ranges provided above, a daily dosage amount and average dosage interval effective to provide a $C_{max}/C_{min}$ ratio not greater than about 5, for example not greater than about 3, at steady-state.

It will be understood that longer dosage intervals will tend to result in greater $C_{max}/C_{min}$ ratios. Illustratively, at steady-state, an Compound 1 $C_{max}$ of about 3 to about 8 µg/ml and $C_{min}$ of about 1 to about 5 µg/ml can be targeted by the present method.

A daily dosage amount effective to maintain a therapeutically effective Compound 1 plasma level is, according to the present embodiment, about 50 to about 1000 mg. In most cases a suitable daily dosage amount is about 200 to about 400 mg. Illustratively, the daily dosage amount can be for example about 50, about 100, about 150, about 200, about 250, about 300, about 350, about 400, about 450, about 500, about 750 or about 1000 mg.

An average dosage interval effective to maintain a therapeutically effective Compound 1 plasma level is, according to the present embodiment, about 3 hours to about 7 days. In most cases, a suitable average dosage interval is about 8 hours to about 3 days, or about 12 hours to about 2 days. A once-daily (q.d.) administration regimen is often suitable.

As in other embodiments, administration according to the present embodiment can be with or without food, i.e., in a non-fasting or fasting condition. It is generally preferred to administer the present compositions to a non-fasting patient.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above described methods and/or compositions without departing from the scope of the disclosure, it is intended that all matter contained in the above description and shown in the accompanying figures shall be interpreted as illustrative and not be viewed in a limiting sense.

What is claimed is:

1. A compound 4-(4-{[2-(4-chlorophenyl)-4,4-dimethyl-cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (Compound 1) in a crystalline form wherein the crystalline form is Compound 1 free base anhydrate, characterized by a powder X-ray diffraction pattern having five or more peaks selected from those at 6.3, 7.1, 9.0, 9.5, 12.5, 14.5, 14.7, 15.9, 16.9, and 18.9 degrees 2θ (pattern A), each peak being ±0.2 degrees 2θ, when measured at about 25° C. with Cu $K_\alpha$ radiation at 1.54178 Å.

2. A pharmaceutical composition comprising the compound in said crystalline form of claim 1 and one or more pharmaceutically acceptable excipients.

3. A process for preparing a pharmaceutical solution comprising dissolving the compound in said crystalline form of claim 1 in a pharmaceutically acceptable solvent or mixture of solvents.

* * * * *